(12) United States Patent
Wallach et al.

(10) Patent No.: US 11,598,782 B2
(45) Date of Patent: Mar. 7, 2023

(54) BIOMARKERS AND METHODS FOR DETECTION OF SEIZURES AND EPILEPSY

(71) Applicant: EVOGEN, INC., Overland Park, KS (US)

(72) Inventors: Todd Wallach, Overland Park, KS (US); Peter Crino, Overland Park, KS (US); John Pollard, Overland Park, KS (US); Elizabeth Brand, Overland Park, KS (US); Maura Strauman, Overland Park, KS (US); Christopher Hollenbeak, Overland Park, KS (US); Rich St. Clair, Overland Park, KS (US); Jeffrey Botbyl, Overland Park, KS (US); John Gledhill, Overland Park, KS (US)

(73) Assignee: Cognizance Biomarkers, LLC, Miami, FL (US)

( * ) Notice: Subject to any disclaimer, the term of this patent is extended or adjusted under 35 U.S.C. 154(b) by 0 days.

(21) Appl. No.: 16/893,266

(22) Filed: Jun. 4, 2020

(65) Prior Publication Data
US 2020/0300871 A1 Sep. 24, 2020

Related U.S. Application Data

(63) Continuation of application No. 16/067,983, filed as application No. PCT/US2017/012094 on Jan. 4, 2017, now abandoned.

(60) Provisional application No. 62/274,578, filed on Jan. 4, 2016, provisional application No. 62/274,551, filed on Jan. 4, 2016.

(51) Int. Cl.

| | | |
|---|---|---|
| *G01N 33/68* | (2006.01) | |
| *A61K 31/4166* | (2006.01) | |
| *A61K 31/55* | (2006.01) | |
| *A61K 31/195* | (2006.01) | |
| *A61K 31/53* | (2006.01) | |
| *A61K 31/551* | (2006.01) | |
| *A61K 31/27* | (2006.01) | |
| *A61K 31/515* | (2006.01) | |
| *A61K 31/4015* | (2006.01) | |
| *A61K 31/20* | (2006.01) | |
| *A61K 31/513* | (2006.01) | |
| *A61K 31/5513* | (2006.01) | |

(52) U.S. Cl.
CPC ....... *G01N 33/6896* (2013.01); *A61K 31/195* (2013.01); *A61K 31/20* (2013.01); *A61K 31/27* (2013.01); *A61K 31/4015* (2013.01); *A61K 31/4166* (2013.01); *A61K 31/513* (2013.01); *A61K 31/515* (2013.01); *A61K 31/53* (2013.01); *A61K 31/55* (2013.01); *A61K 31/551* (2013.01); *A61K 31/5513* (2013.01); *G01N 2800/2857* (2013.01)

(58) Field of Classification Search
CPC ....... G01N 33/6896; G01N 2800/2857; A61K 31/195; A61K 31/513
See application file for complete search history.

(56) References Cited

U.S. PATENT DOCUMENTS

| 9,983,219 B2 | 5/2018 | Pollard et al. |
| 2009/0169619 A1 | 7/2009 | Gande et al. |
| 2013/0331329 A1 | 12/2013 | Pollard et al. |

FOREIGN PATENT DOCUMENTS

WO 2006/019978 A1 2/2006

OTHER PUBLICATIONS

Supplementary European Search Report for Application No. EP 17 73 6215, dated May 29, 2019, 12 pages.
Pollard, John R. et al.: "The TARC/sICAM5 Ratio in Patient Plasma is a Candidate Biomarker for Drug Resistant Epilepsy", Frontiers in Neurology, vol. 3, Jan. 2013, pp. 1-8, XP055397291.
Chen, D. K. et al.: "Use of serum prolactin in diagnosing epileptic seizures: Report of the therapeutics and technology assessment subcommittee of the American Academy of Neurology", Neurology, vol. 65, No. 5, Sep. 12, 2005, pp. 668-675, XP002791087.
Gaillard, William D. et al.: "Epilepsy imaging study guideline criteria: commentary on diagnostic testing study guidelines and practice parameters.", NIH Public Access Author Manuscript, vol. 52, No. 9, Sep. 2011, pp. 1-12, XP002791088.
Maldonado, M. et al.: "Expression of ICAM-1, TNF-[alpha], NF [kappa] B, and MAP kinase in tubers of the tuberous sclerosis complex", Neurobiology of Disease, vol. 14, No. 2, Nov. 2003, pp. 279-290, XP002791089.
Office action dated Apr. 30, 2019 for Canadian Patent Application No. 3,010,221 (6 pages).
Office action dated Jul. 13, 2020 for Canadian Patent Application No. 3,010,221 (6 pages).
Office action dated Apr. 21, 2021 for Chinese Patent Application No. 201780014371.7 (18 pages).
Notice of Reasons for Rejection dated May 25, 2021 for Japanese Patent Application No. 2018-553856 (15 pages).

(Continued)

*Primary Examiner* — Olga N Chernyshev
(74) *Attorney, Agent, or Firm* — Viksnins Harris Padys Malen LLP

(57) ABSTRACT

Epileptic seizures are difficult to diagnose and are often difficult to distinguish from several conditions with similar presentations, and therefore, diagnosis of seizures is often a long, expensive, and unreliable process. This invention provides biomarkers for identifying seizures and epilepsy, assays for measuring and assessing biomarker concentration, predictive models based on biomarkers and computer systems for detecting, assessing and diagnosing phasic and tonic changes associated with seizures and epilepsy in all clinical and healthcare settings. Diagnostic methods, kits and predictive models provided herein provide quantitative and/or qualitative assessment in order to allow patients to proceed immediately to diagnostic and/or treatment protocols, and assess therapeutic treatment effectiveness.

7 Claims, 11 Drawing Sheets

(56) References Cited

OTHER PUBLICATIONS

Notice of Reasons for Rejection dated Jun. 18, 2021 for Japanese Patent Application No. 22020-126628 (3 pages).

| Epileptic Seizures (ES) | Non-Epileptic Seizures (NES) | No Seizures (NS) |
|---|---|---|
| • Seizures in patients whose brains demonstrate a pathologic and enduring tendency to have recurrent seizures[1]<br>• Patients who have experienced at least two unprovoked seizures at least 24 hours apart<br>• Patients who have experienced a single unprovoked seizure and are as likely to experience additional seizures (for example, patients who have experienced a single seizure subsequent to a remote brain insult, like a stroke)<br>• Diagnosis of an unresolved epilepsy syndrome | • Seizures that are secondary to a transient factor<br>• Transient factor acting on an otherwise normal brain to temporarily lower the seizure threshold<br>• Examples include seizures in the context of fever or alcohol withdrawal[1] | • No seizure-like events, or events that mimic seizures<br>• Explained by specific medical and psychological conditions<br>• Examples include TIA, vertigo, panic attacks, and conversion disorder/ psychogenic spells |

[1] ILAE Official Report: A practical clinical definition of epilepsy. Epilepsia, 55(4) 475-482, 2014

FIG. 1

BIOMARKERS AND METHODS FOR DETECTION OF SEIZURES AND EPILEPSY

CROSS-REFERENCE TO RELATED APPLICATIONS

This application claims the benefit of U.S. Provisional Application No. 62/274,551, filed Jan. 4, 2016, and U.S. Provisional Application No. 62/274,578, filed Jan. 4, 2016, the entireties of which are incorporated herein by reference.

GOVERNMENT SUPPORT

This invention was made with Government support under Grant No. 1R43NS079029-01A1, awarded by the National Institutes of Health. The Government may have certain rights in the invention.

FIELD OF THE INVENTION

Epileptic seizures are difficult to diagnose and are often difficult to distinguish from several conditions with similar presentations, and therefore, diagnosis of seizures is often a long, expensive, and unreliable process. Predictive Models (EvoScore™) give clinicians the ability to quickly triage patients by ruling out epilepsy. Predictive Models will allow patients to proceed immediately to diagnostic protocols that are most likely to result in effective treatment, saving significant time and money and sparing patients from unnecessary tests.

The present teachings are generally directed to biomarkers associated with inflammation and seizures, and methods of characterizing biological conditions by scoring quantitative data sets derived from a subject sample, as well as various other embodiments as described herein.

This application is directed towards a blood test for seizure and epilepsy diagnosis and etiology classification in all clinical settings. In some embodiments, individual and panels/arrays of biomarkers indicative of seizure or a tendency to have seizure are provided, including methods for detecting seizure, methods for assessing the effectiveness of a treatment of seizure, a tendency to have seizure or treatment of any underlying disorder resulting in seizure, and diagnostic kits. In other embodiments, Predictive Models are provided, providing both quantitative and qualitative scores predicting phasic and tonic changes associated with seizures and epilepsy. The score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative."

BACKGROUND OF THE INVENTION

Seizures and epilepsy are very common neurological disorders that are associated with significant morbidity, health care cost, and even mortality. Epilepsy is the fourth most common neurological disorder behind migraine, stroke, and Alzheimer's. Epilepsy is a common neurological affliction affecting over 2.3 million patients in the US and 65 million patients worldwide, with significant financial burden. Current estimates are that epilepsy affects approximately 1% of the world population. The prevalence of total active cases currently being treated for epilepsy is 17.8 million, with India (7.5 million), China (4.9 million), and the US (2.3 million) leading other countries. The financial burden of epilepsy care is substantial with a major expense contributed by tests required for appropriate diagnosis. Estimates are that epilepsy and seizures in the U.S. incurs an estimated annual cost of $17.6 billion in direct and indirect costs. A major limitation in providing care for patients with seizures is the lack of a diagnostic blood test to identify clinical events as seizures as opposed to other disorder such as transient ischemic attacks, fainting, sleep disorders, and psychogenic events.

Epilepsy, defined by spontaneous and recurrent seizures, is a highly prevalent public health problem. Also known as "seizure disorder," epilepsy is not diagnosed until after the patient has had two seizures not caused by a known medical condition. In 70 percent of new cases, no cause is apparent. Approximately, 30-50% of people who have had a single, unprovoked seizure will develop recurrent seizures (epilepsy). One-third of people with epilepsy live with uncontrolled seizures because no available treatment works for them.

While much research has been devoted to developing new anti-epileptic drugs (AEDs), the "gold standard" diagnostic protocol—which often hinges on EEGs—has remained constant and inadequate. When patients present with a suspected seizure, the process to diagnose whether the event was caused by epilepsy or another disorder is most often long and expensive. Patients undergo a lengthy work-up that regularly includes blood tests, imaging studies, EEGs, and video EEGs where available. Often the diagnosis is one of exclusion where other medical conditions are "ruled-out;" and definitive diagnosis of epilepsy is typically made if an EEG records an epileptic seizure "event" while it is occurring, usually during a lengthy and expensive stay in an in-patient epilepsy monitoring unit.

In addition to the high cost associated with a long engagement with the health system, the current state of epilepsy diagnosis presents another critical issue: in the absence of a good triage tool for early diagnosis, patients who experience suspected seizures because of other underlying conditions may be either over- or under-treated erroneously with AEDs, during which time their underlying conditions actually remain untreated while they experience undesirable medication side-effects. Thus, timely diagnosis of the patient's condition (whether epilepsy or not) remains a significant unmet medical need.

Epilepsy Diagnostic Methodologies

Accurately diagnosing epilepsy is very challenging and time consuming because clinicians rarely observe the actual seizure, plus there are many different types of seizures and epilepsy syndromes with differing presentations. Furthermore, other neurological disorders can be mimics for seizures leading to erroneous diagnosis, inappropriate treatments with significant potential adverse events, incorrect prognosis, and significant waste of health care resources. Clinical events such as movement disorders e.g., tremors, tics, dyskinesias, fainting spells/syncope, transient ischemic attacks (TIA), sleep disorders/parasomnias, and somatiform psychiatric disorders can be mistaken for seizures even by seasoned clinicians. Rendering a definitive diagnosis of seizures is critical to long-term patient health and outcome that will lead to early treatment, subsequent follow up and surveillance, counseling, and support. Currently, obtaining a definitive diagnosis of seizures or epilepsy is expensive and inconvenient for patients as it may require inpatient evaluation and a battery of costly tests. The diagnosis of epilepsy has for years relied on a broad costly and often cumbersome medical-neurological evaluation that includes:

The "gold standard" test is electroencephalography (EEG). If a seizure is captured during the recording, seizure activity will appear as rapid spiking waves on the EEG. Brain lesions, i.e., tumors, strokes, may cause slowing of normal electrical brain rhythms. The challenge with EEG is that it is typically performed as a post hoc assay, that is, after the clinical event is finished, and may in fact be normal. A continuous EEG is a 24 hour EEG done in the hospital to get a prolonged pattern and try to "catch" the seizure when occurring. This requires a costly inpatient hospital stay, and there is no way to know for certain that a clinical event will occur during the stay. Obviously, this provides a significant logistical challenge to caregivers in the outpatient and emergency department (ED) settings since most patients come to the ED after the event has ended and only historical information is gathered; definitive diagnosis of a single seizure is essentially impossible and empiric at best. EEG is only about at best 30 to 50% sensitive (measures proportion of positives that are correctly identified) and 50% specific.

Medical History to determine circumstances surrounding first seizure like event, the duration and frequency of the event, and age of onset. Often the patients or caregivers cannot give the level of detail needed for accurate diagnosis. Missing information regularly includes time of onset and duration of event due to the fact that a caregiver was either not present or failed to keep accurate records. Seizure-like events are traumatic events for patients, caregivers, and responders where the first reaction is to care for the patient and not to keep track of timing or other information necessary for diagnosis.

Laboratory studies including complete blood count (CBC), chemistry metabolic panel (CMP), and toxicology screen tests. These do not diagnose the "seizure" itself, but instead may provide clues to explain neurological dysfunction. Measurement of prolactin levels is unreliable. EEG is used to evaluate several types of brain disorders.

MRI is a technique used to create an image or scan of the brain. MRI scans can be used examine a person's brain structure. An MRI scan cannot, by itself, determine whether the person has epilepsy, but when considered with other information, may help the clinician decide if epilepsy is a likely cause of the seizure like events.

PET scan may be used to locate the part of the brain causing seizure like events as it gives clinicians additional information about how the cells in the body are functioning. While PET scans are helpful in some cases, they often show abnormalities that are not related to epilepsy and are less often part of the diagnostic process.

Lumbar puncture is a procedure in which fluid surrounding the spinal cord is withdrawn through needle aspiration and analyzed in the lab. It is performed to rule out infections, such as meningitis or encephalitis, as the cause of seizure like events.

Timely Diagnosis: An Unmet Need

The diagnostic process can take several months before clinical events are pinpointed as epileptic seizures, and often clinical care is largely empiric, based on supporting but not definitive evidence—often resulting in either under- or over-diagnosis and treatment. Thus, timely and accurate seizure diagnosis remains an unmet medical need. Not only is the diagnostic process long, there is a significant burden on the healthcare system with annual figures for epilepsy diagnostic methodologies totaling greater than $15 billion in the US alone. Thus, a critical gap in our clinical assessment of seizures in virtually every clinical setting is an accurate diagnostic blood test for seizures that can be used for either single or recurrent events to identify both phasic and tonic changes in brain activity. Numerous clinical scenarios can be envisioned in which a clinical diagnostic test for seizures would be invaluable to explain a patient's clinical condition: 1) an individual is brought to the ED after collapsing at home; 2) an individual is found confused and wandering in the street; 3) a hospitalized patient has a brief episode of unresponsiveness or change in mental status; 4) patients in third world countries where EEG, CT, or MRI are not readily available. A simple blood test that could provide immediate and definitive explanation of the clinical event with actionable results would be an enormous diagnostic advance and could direct further studies towards ("rule in") or away ("rule out") from epilepsy, saving resources, time, and expense. In short, a simple blood test for seizures would be a major innovation.

Accurately diagnosing epilepsy is very challenging and time consuming because clinicians rarely observe seizures and there are many different types of seizures and epilepsy syndromes with differing presentations. The diagnosis of epilepsy has for years relied on a "gold standard" to include patient medical history (inclusive of complete blood count and chemistry metabolic profile) and electroencephalograph (EEG). Once these are analyzed, the clinician may also perform magnetic resonance imaging (MRI) and continuous video EEG (vEEG) where available. Additional diagnostic techniques may include positron emission tomography (PET) scan and lumbar puncture (spinal tap). A major challenge in the diagnosis of epilepsy using the gold standard EEG is the fact that EEG has a low sensitivity for epilepsy, ranging between 25-56%. Specificity is better, but also variable at 78-98%—as specificity is dependent on the skill of the physician reading the EEG. Additionally, while often adequate for the appropriate diagnosis of a seizure disorder, EEGs can appear persistently normal for patients with epilepsy. In fact, EEG was demonstrated to have a Sensitivity of 37-55%, Specificity of 98-99%, PPV of 98%, and NPV of 64-66% in our studies which validates the need for a test that maximizes sensitivity when diagnosing a seizure.

Importantly, while patients are undergoing months of diagnostic work-up for epilepsy, as described above, they are typically subjected to a period of AED medication trial and error to determine which—if any—medications control their seizures. Especially when considering the side-effect-laden and in some cases teratogenic consequences of AEDs, this unnecessary medication cost is huge and when combined with the long diagnostic process, there is a significant burden on the health care system with annual figures for epilepsy diagnostic methodologies totaling greater than $15 billion in the US alone.

In an effort to streamline epilepsy diagnosis, it has been observed that prolactin levels were elevated subsequent to a seizure. Further clinical evaluation of application of prolactin for seizure diagnosis indicated that prolactin is only a viable biomarker for seizure if a sample is collected between 10 and 20 minutes of a seizure. Additionally, Prolactin is only applicable to a subset of seizures including primary or secondarily generalized tonic-clonic seizures and partial complex seizures of temporal lobe origin. Accordingly, the short window of viability (minutes after), coupled with inadequate diagnostic sensitivity, specificity, and accuracy, preclude prolactin from being a practical seizure biomarker, and is rarely, if ever used today in clinical settings.

Link Between Inflammation and Seizures

Seizures induce an inflammatory response in brain tissue where the seizure starts. For example, there may be a robust inflammatory response in the resected brain specimens of intractable epilepsy patients including expression of critical proinflammatory cytokines and chemokines such as tumor necrosis factor alpha (TNFα, interleukin-8 (IL-8), interleukin-6 (IL-6), and interferon gamma (IFNγ). Increased levels of TNFα, IL-8, IL-6, and IFNγ have also been detected in mouse seizure models highlighting the idea that inflammatory processes in the brain contribute to the pathogenesis of seizures and to the establishment of a chronic epileptic focus. Many of these cytokines have been detected in the cerebrospinal fluid of seizure patients immediately following seizures as well. Expression of several cytokine receptor subtypes is also upregulated on neurons and astrocytes, suggesting a mechanism for activated intracellular signaling, highlighting autocrine and paracrine actions of cytokines in the brain. Functional interactions between cytokines and classical neurotransmitters such as glutamate and GABA suggest the possibility that these interactions underlie established cytokine-mediated changes in neuronal excitability, thus promoting seizures. There is also clear evidence that acute seizures can induce increased blood-brain barrier permeability. The effect has been shown to facilitate passage of activated T-cells and macrophages into brain tissue, facilitating an inflammatory response in the brain, and fostering the leakage of brain specific inflammatory cytokines and chemokines into peripheral blood.

ICAM5 is a neuronal glycoprotein that is exclusively expressed in the brain and functions as an anti-inflammatory protein via inhibition of T cell mobility and chemotaxis. ICAM5 is confined to the soma and dendrites in neurons and it is enriched in dendritic filopodia with less expression in more mature dendritic spines. ICAM5 has a complex structure with nine external immunoglobulin domains followed by a transmembrane and a cytoplasmic domain. The external portions bind to beta1- and beta2-integrins and the matrix protein vitronectin, whereas it's transmembrane domain binds to presenilins and the cytoplasmic domain to alpha-actinin and the ERM family of cytoplasmic proteins. VVhen cleaved and released ICAM5 becomes a soluble form (sICAM5) and can be released into the extracellular space and blood. sICAM5 strongly stimulates neurite outgrowth. In immunoelectron microscopic studies, it was found that ICAM5 was localized at the surface membrane of postsynaptic spines of pyramidal cell dendrites but not at that of axonal terminals in the hippocampal CA1 region. Long-term potentiation (LTP) at Schaffer collateral-CA1 synapses in the hippocampus was suppressed by blocking of ICAM5 with anti-ICAM5 antibodies or recombinant sICAM5 protein. These observations suggest a role for sICAM5-mediated cell-cell interactions as a key step in the development of LTP. Subsequent studies showed that sICAM5 may act as a major adhesion molecule for leukocyte binding to neurons in the brain. In one small cohort, increased levels of sICAM5 were reported in the cerebrospinal fluid and serum of patients with temporal lobe epilepsy with no changes reported in multiple sclerosis or Alzheimer's disease. Activation of NMDA receptors promotes dendritic spine development through metalloproteinase (MMP)-mediated ICAM-5 cleavage and contributes to neuronal excitability. Additionally, it was demonstrated that sICAM5 plays a critical role in modulating chemokine production in the brain in a mouse model of encephalitis. The ICAM-5 ectodomain was found to stimulate an increase in the frequency, but not the amplitude, of AMPA mini excitatory post-synaptic currents (mEPSCs) using single cell recordings. Using biotinylation and precipitation assays, it has been found that the ICAM-5 ectodomain causes an increase in membrane levels of GluA1, but not GluA2, AMPAR subunits. An ICAM-5 associated increase in GluA1 phosphorylation was found. At the same time, ICAM-5 causes an increase in GluA1 surface staining along dendrites without causing an increase in dendritic spine number. This suggested that sICAM-5 increases glutamatergic transmission and could be affected by brain network activity changes.

TARC (Thymus and activation-regulated chemokine; CCL17) is a chemokine (i.e., cytokine that is responsible for the movement of T and B lymphocytes, monocytes, neutrophils, eosinophils and basophils, in allergic and other inflammatory conditions) that principally expressed in the thymus and blood mononuclear cells. TARC functions as a proinflammatory cytokine and lymphocyte chemoattractor that binds specifically to CCR4 receptors on T-cells and induces chemotaxis in T-cell lines. Since TARC binds to CCR4, it is considered a Th2 type chemokine. TARC is produced by multiple cell types including dendritic cells, endothelial cells, keratinocytes and fibroblasts. Serum TARC levels have been shown to be a useful assay for disease activity in atopic dermatitis, an inflammatory disorder of the skin affecting children and adults. Indeed, TARC is an established systemic rheostat for inflammation. TARC exhibits low-level expression in the choroid plexus in the brain but has minimal expression by neurons or astrocytes. However, little is known about changes in plasma TARC expression as a consequence of seizures.

TNF-α is a secreted cytokine that has been implicated in a range of neurological disorders including stroke, Alzheimer's disease, cancer, and autism. A number of studies have examined TNFα levels in both experimental epilepsy model systems as well as human samples including CSF and serum. Kainate induced seizures in the rat induce TNF-α expression in hippocampus. In dogs with spontaneous seizures, TNF-α levels are elevated in CSF and manipulation of TNF-α signaling cascades in mouse seizure models can attenuate seizure. TNF-α levels are robustly elevated in patients with temporal lobe epilepsy suggesting it is a broad marker of inflammation in the brain, especially in the setting of seizures.

As shown herein, the described invention ameliorates the deficiencies in the field. Indeed, based on a link between inflammation and seizures both in experimental models and in humans with epilepsy, an initial proteomics screen in patient plasma was used to probe a panel of biomarkers linked to inflammatory cytokines that were hypothesized to exhibit phasic or tonic changes in response to seizures in our studies. It was speculated that measurable changes in levels of specific plasma proteins could yield a diagnostic blood test for seizures. Plasma samples were analyzed by multiplex ELISA at baseline (pre-seizure) and 24 hours post-seizure (documented in the EMU by EEG recording) in a cohort of 20 epilepsy patients. It was found that the ratio of Thymus and Activation Regulated Chemokine (TARC or CCL17) to soluble isoform of Intercellular Adhesion Molecule 5 (sICAM5 or telencephalin) was statistically different in seizure patients compared with normal controls. Subsequently, it was found that plasma TNFα levels were also statistically significantly different in patients who have suffered a seizure compared with control individuals. In another cohort of 131 neurology patients admitted to the Epilepsy Monitoring Unit and 30 normal controls, patient samples were analyzed both pre-seizure and 1 minute to over 72 hours post-seizure, and an algorithm involving TNFα, TARC and sICAM5 was devised that can distinguish between epileptic and non-epileptic event plasma samples.

SUMMARY OF THE INVENTION

In an embodiment, the invention includes EvoScore, a blood based diagnostic test, that effectively screens plasma from patients to identify measurable changes in select proteins following seizures. Three proteins linked to inflammatory processes, TARC, sICAM5, and TNF-α are used to generate, a predictive algorithm with associated score (EvoScore Predictive Models™) that can be translated into a diagnostic test for seizures. The algorithm, which combines protein levels with patient demographic characteristics has demonstrated, with strong diagnostic performance, predictions of both phasic and tonic changes (acute and chronic) in patients with seizures and epilepsy—both ruling out patients and ruling in patients with seizures and epilepsy, with the ability to monitor patients over time and over the course of treatment. EvoScore can be used in all clinical and healthcare settings.

In an embodiment, the invention includes a method for diagnosing epilepsy and/or a seizure in a mammalian subject. In some embodiments, the method may include the step of contacting a blood plasma or blood serum sample obtained from the mammalian subject with a diagnostic reagent that can measure or detect the expression level of soluble ICAM-5 (sICAM-5). In some embodiments, the method may include the step of contacting said blood plasma or blood serum sample obtained from the mammalian subject with a diagnostic reagent that can measure or detect the expression level of TARC. In some embodiments, the method may include the step of contacting said blood plasma or blood serum sample obtained from the mammalian subject with a diagnostic reagent that can measure or detect the expression level of TNF-α. In some embodiments, the method may include the step of comparing the concentrations of sICAM5, TARC and TNF-α to normal control concentrations. In some embodiments, the method may include the step of comparing concentration ratios of sICAM5, TARC and TNF-α to normal control concentration ratios. In some embodiments, the method may include the step of diagnosing epilepsy in the mammalian subject.

In an embodiment, the invention includes a method for diagnosing epilepsy and/or a seizure in a mammalian subject that may include the step of contacting a blood plasma or blood serum sample obtained from the mammalian subject with a diagnostic reagent that can measure or detect the expression level of TARC. In some embodiments, the method may include the step of contacting said blood plasma or blood serum sample obtained from the mammalian subject with a diagnostic reagent that can measure or detect the expression level of TNF-α. In some embodiments, the method may include the step of comparing the concentrations of TARC and TNF-α to normal control concentrations. In some embodiments, the method may include the step of comparing concentration ratios of TARC and TNF-α to normal control concentration ratios. In some embodiments, the method may include the step of diagnosing epilepsy in the mammalian subject.

In an embodiment, the invention includes a kit for generating quantitative data for a patient. In some embodiments, the kit may include a diagnostic reagent that can measure an expression level of soluble ICAM-5 (sICAM-5) in a blood plasma or blood serum sample taken from the patient. In some embodiments, the kit may include a diagnostic reagent that can measure an expression level of TARC in the blood plasma or blood serum sample taken from the patient. In some embodiments, the kit may include a diagnostic reagent that can measure an expression level of TNF-α in the blood plasma or blood serum sample taken from the patient. In some embodiments, the kit may include an analysis unit for comparison of the expression levels of sICAM-5, TARC, and TNF-α to expression levels of normal controls.

In an embodiment, the invention includes a system for scoring a sample, said system comparing expression levels of sICAM5, TARC and TNF-α to determine epilepsy from normal controls.

In an embodiment, the invention includes a computer having software, with said software comparing expression levels of sICAM5, TARC and TNF-α to determine epilepsy from normal controls.

In an embodiment, the invention includes a method of treating a seizure disorder in a patient with altered blood plasma or blood serum expression levels of sICAM5, TARC, and TNF-α, or a ratio of a combination thereof, relative to a normal control, the method including administering a therapy for epilepsy to the patient.

BRIEF DESCRIPTION OF THE DRAWINGS

The foregoing summary, as well as the following detailed description of the invention, will be better understood when read in conjunction with the appended drawings.

FIG. 1 illustrates criteria for different types of seizures.

DETAILED DESCRIPTION OF THE INVENTION

Figure 2:
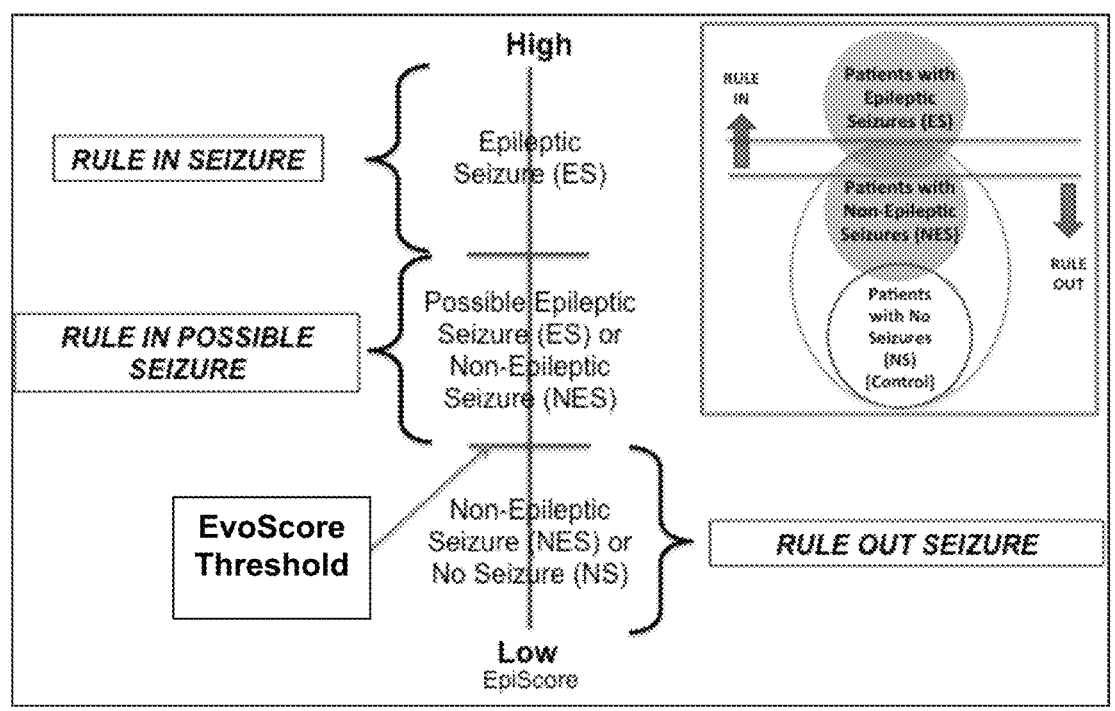
FIG. 2 illustrates the objectives of the algorithm and ultimate actionable results.

In epilepsy an immune response is generated within the region of seizure onset. In several distinct tissue lesion types such as tuberous sclerosis (TSC) and mesial temporal sclerosis (MTS), pro-inflammatory cytokines such as IL-1p, IL-6, TNF-α, Fas, and Fas-ligand are activated. In addition, there is complement fixation and deposition, altered blood-brain barrier permeability, and macrophage infiltration. Inflammation may generate a wide variety of downstream effects including upregulation of IL-1β production, activation of TLR4, NFκB, mTOR, and MAPK cascades, attraction of activated lymphocytes, microglia, and macrophages, and alteration of astrocyte physiology. Additionally, the relative balance with anti-inflammatory cytokines can also be modulated, demonstrating a change in levels of cytokines like IL-4, IL-10 and IL-13 Without being bound by theory, these changes may be a result of a disease process leading to seizures, caused by seizures, and/or be the result of seizures (see FIG. 1). Diagnostic tests and algorithms developed are able to distinguish seizures from not, and epilepsy from normal (see FIG. 2) The present application addresses a need in the art for markers associated with seizures.

As used herein, the abbreviations "A1AT" and "a1AT" refer to alpha 1-antitrypsin, also known as serpin peptidase inhibitor, clade A (alpha-1 antiproteinase, antitrypsin), member 1.

The terms "comprising" and "including" are used interchangeably, unless otherwise noted.

The term "cryptogenic" is used herein to refer to a seizure or epilepsy of unknown origin.

The term "phasic" is used herein to refer to a change in blood biomarkers directly related to an immediate or sudden event or seizure. The change in the blood is short-lived and resolves within a specific period of time after the event.

The term "tonic" is used herein to refer to persistent or constantly changes in blood biomarkers related to a patient's over-arching condition. The levels are distinguishable from those in control subjects and do not fluctuate markedly based on whether the patient has experienced an event symptomatic of his or her condition.

The term "acute" is used herein to refer to a change in blood biomarkers directly related to an immediate or sudden event or seizure. The change in the blood is short-lived and resolves within a specific period of time after the event.

The term "chronic" is used herein to refer to persistent or constantly changes in blood biomarkers related to a patient's over-arching condition. The levels are distinguishable from those in control subjects and do not fluctuate markedly based on whether the patient has experienced an event symptomatic of his or her condition.

The terms "disease", "disorder", or "condition" are used herein to refer to any manifestations, symptoms, or combination of manifestations or symptoms, recognized or diagnosed as leading to, causing, or influencing seizure. The terms include, but are not limited to, traumas, inflammatory and autoimmune responses, physiological malformations, and genetic defects.

The abbreviation "GM-CSF" refers to granulocyte-macrophage colony-stimulating factor.

The abbreviation "HGF" refers to hepatocyte growth factor.

The abbreviation "ICAM-1" refers to intercellular adhesion molecule 1.

The term "ictal" refers to a physiologic state or event such as a seizure.

The term "indicative" (or "indicative of") encompasses both prediction (including tendency), and detection (proximate to the occurrence of a seizure), and unless otherwise noted, embodiments encompassing the term are intended to define and encompass embodiments specific to prediction, specific to detection, and for prediction as well as for detection of a past or current event. Use of the term indicative in conjunction with the term "tendency" is intended solely for emphasis of evidence of a past event versus a tendency toward a future event, but the use solely of indicative is intended to encompass tendency unless otherwise indicated.

The abbreviation "BDNF" refers to brain-derived neurotrophic factor.

The abbreviation "MCP-1" refers to monocyte chemotactic protein-1, also known as chemokine (C-C motif) ligand 2 (CCL2), or variants thereof.

The abbreviation "MDC" refers to macrophage derived cytokine, also known as C-C motif chemokine 22 (CCL-22), or variants thereof.

The abbreviation "MIP-1β" refers to macrophage inflammatory protein-1β, also known as chemokine C-C motif ligand 4 (CCL-4), or variants thereof.

The abbreviation "IP-10" refers to interferon gamma-induced protein 10, small-inducible cytokine B10, C-X-C motif chemokine 10 (CXCL10), or variants thereof.

Eotaxin, also known as eotaxin-1, refers to chemokine (C-C motif) ligand 11 (CCL11), or variants thereof.

Eotaxin-3 refers to chemokine (C-C motif) ligand 26 (CCL26), or variants thereof.

The term "sample" is used herein to refer to a blood plasma or blood serum sample, unless otherwise noted. In each embodiment described herein, the use of blood plasma is contemplated as an independent embodiment from the alternative of blood plasma or blood serum. In each embodiment described herein, the use of blood serum is contemplated as an independent embodiment from the alternative of blood plasma or blood serum. In each embodiment described herein, the use of another biological sample, including but not limited to cerebrospinal fluid (CSF), a tissue sample obtained by resection, saliva, and urine is contemplated according to conventional techniques in the art for obtaining the sample and for analysis of same. The sample can be treated prior to use, such as preparing plasma from blood, diluting viscous fluids, and the like. Methods of treatment can involve filtration, distillation, extraction, concentration, inactivation of interfering components, the addition of reagents, and the like.

The terms "seizure" and "epilepsy" are used interchangeably, two unprovoked seizures being required for a clinical diagnosis of epilepsy, unless otherwise noted. The term epilepsy may also be defined by the understanding of, or theories of, seizure as understood as of the time of filing of the application. Epilepsy includes and is not limited to all forms of epilepsy.

The terms "subject", "individual", and "patient" are used interchangeably herein to refer to a mammal from which a sample is taken, unless otherwise noted. The terms are intended to encompass embodiments specific to humans. A subject, individual or patient may be afflicted with, at risk for, or suspected of having a tendency to have seizure or a disorder for which seizure is symptomatic. The term also includes domestic animals bred for food or as pets, including horses, cows, sheep, pigs, cats, dogs, and zoo animals. Typical subjects for treatment include persons susceptible to, suffering from or that have suffered one or more seizures. In particular, suitable subjects for treatment in accordance with the invention are persons that are susceptible to or that have suffered one or more seizures.

The abbreviation "TARO" refers to 'thymus and activation regulated chemokine', and is used interchangeably herein with chemokine (C-C motif) ligand 17 (CCL17).

The terms "telencephalin", "TLN", "ICAM-5", and "ICAM5" are used interchangeably herein.

The term "tendency", e.g., "tendency to have seizure", is intended to refer to a reasonable medical probability of an event, e.g., seizure to occur or recur. The term also encompasses the frequency with which such events may occur before, after, or during ongoing treatment.

As used herein, the term "treat" or "treating" refers to any method used to partially or completely alleviate, ameliorate, relieve, inhibit, prevent, delay onset of, reduce severity of and/or reduce incidence of one or more symptoms or features of a particular condition, in any clinical setting e.g., seizure or a seizure-related disorder. Treatment may be administered to a subject who does not exhibit signs of a condition and/or exhibits only early signs of the condition for the purpose of decreasing the risk of developing pathology associated with the condition. Thus, depending on the state of the subject, the term in some aspects of the invention may refer to preventing a condition, and includes preventing the onset, or preventing the symptoms associated with a condition. The term also includes maintaining the condition and/or symptom such that the condition and/or symptom do not progress in severity. A treatment may be either performed in an acute or chronic way. The term also refers to reducing the severity of a condition or symptoms associated with such condition prior to affliction with the condition. Such prevention or reduction of the severity of a condition prior to affliction refers to administration of a therapy to a subject that is not at the time of administration afflicted with the condition. Preventing also includes preventing the recurrence of a condition, frequency thereof, or of one or more symptoms associated with such condition. The terms "treatment" and "therapeutically" refer to the act of treating, as "treating" is defined above. The purpose of intervention is to combat the condition and includes the administration of therapy to prevent or delay the onset of the symptoms or complications, or alleviate the symptoms or complications, or eliminate the condition. For example, a treatment may be used to ameliorate symptoms or frequency thereof (e.g., frequency of seizure) associated with a disorder.

The terms "tuberous sclerosis", "tuberous sclerosis complex", and the abbreviation/acronyms "TS" and "TSC", are used interchangeably herein.

The abbreviation "VCAM-1" refers to vascular cell adhesion molecule 1.

The abbreviation "VEGF-A" refers to vascular endothelial growth factor A.

sICAM5

ICAM-5 is a neuron-derived protein differentially distributed in the blood plasma or blood serum of epilepsy patients relative to healthy patients. Soluble ICAM-5 (also known as sICAM5, sICAM-5, or variants thereof) is cleaved from ICAM-5 by metalloproteases in response to inflammation. Unexpectedly, it is found that altered sICAM-5 expression is found in the case of seizure patients relative to healthy patients. sICAM- and/or in combination, the sICAM-5/TARC and/or sICAM5/TNF-α ratio is altered over healthy control.

In one embodiment, a polypeptide expression panel or array is provided, the panel or array comprising a probe capable of binding soluble ICAM-5 (sICAM-5) in blood plasma or blood serum of a mammalian subject, wherein an altered plasma or serum concentration of sICAM-5 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

TARC

TARC is also an effective marker, differentially distributed in the blood plasma or blood serum of epilepsy patients relative to healthy patients and it is shown to be elevated in seizure patients. In an embodiment, TARC and/or in combination, the sICAM-5/TARC and/or TNF-α/TARC ratio is altered over healthy control.

In another embodiment, a polypeptide expression panel or array is provided, the panel or array comprising a probe capable of binding TARC in blood plasma or blood serum of a mammalian subject, wherein an altered plasma or serum concentration of TARC relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

TNF-α

TNF-α is also an effective marker, differentially distributed in the blood plasma or blood serum of epilepsy patients relative to healthy patients and it is shown to be elevated in seizure patients. In an embodiment, TNF-α and/or the sICAM-5/TNF-α and/or TNF-α/TARC ratio is altered over healthy control.

In another embodiment, a polypeptide expression panel or array is provided, the panel or array comprising a probe capable of binding TNF-α in blood plasma or blood serum of a mammalian subject, wherein an altered plasma or serum concentration of TNF-α relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

sICAM5 and TARC

Also provided is a polypeptide or array comprising a probe capable of binding sICAM-5 in blood plasma or blood serum and a probe capable of binding TARC in blood plasma or blood serum of a mammalian subject, wherein a change in plasma or serum concentration of sICAM-5 and/or with a change in plasma or serum concentration of TARC relative to a healthy control indicates seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

sICAM5 and TNF-α

Also provided is a polypeptide or array comprising a probe capable of binding sICAM-5 in blood plasma or blood serum and a probe capable of binding TNF-α in blood plasma or blood serum of a mammalian subject, wherein a change in plasma or serum concentration of sICAM-5 and/or with a change in plasma or serum concentration of TNF-α (relative to a healthy control) indicates seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

TARC and TNF-α

Also provided is a polypeptide or array comprising a probe capable of binding TARC in blood plasma or blood serum and a probe capable of binding TNF-α in blood plasma or blood serum of a mammalian subject, wherein a change in plasma or serum concentration of TARC and/or with a change in plasma or serum concentration of TNF-α (relative to a healthy control) indicates seizure or a tendency to have seizure. The concentration may be taken as numerical or logarithmic in a predictive model.

Individual measurements may be taken and analyzed individually or in any combination using linear or logarithmic units, or by using ratios of linear or logarithmic units. The reciprocals of ratios of linear or logarithmic units may also be used.

sICAM5, TARC and TNF-α

Also provided is a polypeptide or array comprising a probe capable of binding sICAM-5 in blood plasma or blood serum and a probe capable of binding TARC in blood plasma or blood serum and a probe capable of binding TNF-α in blood plasma or blood serum of a mammalian subject, wherein a change in plasma or serum concentration of sICAM-5 and/or with a change in plasma or serum concentration of TARC and/or a change in plasma or serum concentration of TNF-α (relative to a healthy control) indicates seizure or a tendency to have seizure.

In another embodiment, a method for predicting or detecting seizure is provided, comprising contacting a blood plasma or blood serum sample obtained from a mammalian subject with a diagnostic reagent that can measure or detect the expression level of soluble ICAM-5 (sICAM-5) and contacting a blood plasma or blood serum sample obtained from a mammalian subject with a diagnostic reagent that can measure or detect the expression level of TARC, and contacting a blood plasma or blood serum sample obtained from a mammalian subject with a diagnostic reagent that can measure or detect the expression level of TNF-α, taken individually, combined (any two of the markers) or all three taken together collectively a change plasma or serum concentration of sICAM-5 and/or with a change plasma or serum concentration of TARC and/or a change plasma or serum concentration TNF-α relative to a healthy control indicates a seizure having occurred or a tendency to have seizure.

Individual measurements may be taken and analyzed individually or in any combination using linear or logarithmic units, or by using ratios of linear or logarithmic units. The reciprocals of ratios of linear or logarithmic units may also be used.

sICAM5/TARC Ratio

In further embodiments, a polypeptide or array comprising a probe capable of binding sICAM-5 in blood plasma or blood serum and a probe capable of binding TARC in blood plasma or blood serum of a mammalian subject, wherein a change in plasma or serum concentration of sICAM-5 and/or with a change in plasma or serum concentration of TARC and/or the change of the ratio of sICAM-5/TARC in tested subjects relative to control (healthy, non-epileptic/non-seizure) is altered relative to healthy controls and is indicative of a seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

sICAM5/TNF-α Ratio

In further embodiments, a polypeptide or array comprising a probe capable of binding sICAM-5 in blood plasma or blood serum and a probe capable of binding TNF-α in blood plasma or blood serum of a mammalian subject, wherein a change in plasma or serum concentration of sICAM-5 and/or with a change in plasma or serum concentration of TNF-α and/or with the change of the ratio of sICAM5/TNF-α in tested subjects relative to control (healthy, non-epileptic/non-seizure) is altered relative to healthy controls and is indicative of a seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

TARC/TNF-α Ratio

In further embodiments, a polypeptide or array comprising a probe capable of binding TARC in blood plasma or blood serum and a probe capable of binding TNF-α in blood plasma or blood serum of a mammalian subject, wherein a change in plasma or serum concentration of TARC in and/or with a change in plasma or serum concentration of TNF-α and/or a change in plasma or serum concentration of TNF-α the change of the ratio of TNF-α/TARC in tested subjects relative to control (healthy, non-epileptic/non-seizure) is altered relative to healthy controls and is indicative of a seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

Combination of Ratios

In further embodiments, a polypeptide or array comprising a probe capable of binding sICAM-5 in blood plasma or blood serum and a probe capable of binding TARC in blood plasma or blood serum and a probe capable of binding TNF-α in blood plasma or blood serum of a mammalian subject, wherein a change in plasma or serum concentration of sICAM-5 and/or with a change in plasma or serum concentration of TARC and/or a change in plasma or serum concentration of TNF-α and/or with the change of the ratio of sICAM-5/TARC, and/or TNF-α/TARC and/or sICAM5/TNF-α in tested subjects relative to control (healthy, non-epileptic/non-seizure) is altered relative to healthy controls and is indicative of a seizure or a tendency to have seizure. The ratio may be used as linear or logarithmic units, and/or may be used as a reciprocal, in a predictive model.

Combination of Individual Measures and Ratios

In further embodiments, a polypeptide or array comprising a probe capable of binding sICAM-5 in blood plasma or blood serum and a probe capable of binding TARC in blood plasma or blood serum and a probe capable of binding TNF-α in blood plasma or blood serum of a mammalian subject, wherein a change in plasma or serum concentration of sICAM-5 and/or with a change in plasma or serum concentration of TARC and/or a change in plasma or serum concentration of TNF-α the change of the ratio of sICAM-5/TARC, and/or TNF-α/TARC and/or sICAM5/TNF-α in tested subjects relative to control (healthy, non-epileptic/non-seizure) is altered relative to healthy controls and is indicative of a seizure or a tendency to have seizure. Any combinations of individual concentrations and ratios may be used.

Individual measurements may be taken and analyzed individually or in any combination using linear or logarithmic units, or by using ratios of linear or logarithmic units. The reciprocals of ratios of linear or logarithmic units may also be used.

Patient Demographic Characteristics

In another embodiment, when combined any biomarkers concentrations for sICAM5, TARC and TNF-α and/or any combination of ratios of biomarker concentrations for sICAM-5/TARC, and/or TNF-α/TARC and/or sICAM5/TNF-α, patient demographics or other characteristics associated with the patient, including but not limited to age, sex and/or race may indicate a seizure having occurred or a tendency to have a seizure in comparison to relative normal or healthy controls.

When combined with patient demographic characteristics, the individual measurements may be taken and analyzed individually or in any combination using linear or logarithmic units, or by using ratios of linear or logarithmic units. The reciprocals of ratios of linear or logarithmic units may also be used.

Other BioMarkers

ICAM-5 is a neuron-derived protein differentially distributed in the blood plasma or blood serum of epilepsy patients relative to healthy patients. Soluble ICAM-5 (also known as sICAM5, sICAM-5, or variants thereof) is cleaved from ICAM-5 by metalloproteases in response to inflammation. Unexpectedly, it is found that altered sICAM-5 expression is found in the case of seizure patients relative to healthy patients. And/or the sICAM-5/TARC and/or sICAM5/TNF-α ratio is altered over healthy control Additional markers that are useful include, alone or in combination, IL-1 3, IL-2, IL-8, and IFN-γ. Still additional markers that are useful include, alone or in combination, IL-6, IL-10, IL-12 p70, Fas, Fas-ligand, MCP-1, MDC, MIP-1β, GM-CSF, MCP-4, IP-10, BDNF, Eotaxin-3, Eotaxin, TARC, TNF-α, substance P and prostaglandin $E_2$, nerve growth factor (NGF), CCL-5 (RANTES), monocyte chemoattractant protein (MCP-1), monocyte inflammatory protein (MIP-1α). Probes may further include, alone or in combination, α1AT, VCAM-1, ICAM-1, HGF, and VEGF-A. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

TARC is also an effective marker, differentially distributed in the blood plasma or blood serum of epilepsy patients relative to healthy patients and it is shown to be elevated in seizure patients. TARC and/or the sICAM-5/TARC and/or TNF-α/TARC ratio is altered over healthy control. Additional markers that are useful include, alone or and/or in combination, IL-1β, IL-2, IL-8, and IFN-γ. Still additional markers that are useful include, alone or in combination, IL-10, IL-12 p70, Fas, Fas-ligand, MCP-1, MDC, MIP-1β, GM-CSF, MCP-4, IP-10, BDNF, Eotaxin-3, Eotaxin, and TNF-α. Probes may further include α1AT, VCAM-1, ICAM-1, HGF, and VEGF-A. Probes may also include those for components of the complement cascade, e.g., C1q, C3c and C3d. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

TNF-α is also an effective marker, differentially distributed in the blood plasma or blood serum of epilepsy patients relative to healthy patients and it is shown to be elevated in seizure patients. TNF-α and/or the sICAM-5/TNF-α and/or TNF-α/TARC ratio is altered over healthy control. Additional markers that are useful include, alone or in combination, IL-1β, IL-2, IL-8, and IFN-γ. Still additional markers that are useful include, alone or in combination, IL-10, IL-12 p70, Fas, Fas-ligand, MCP-1, MDC, MIP-1β, GM-CSF, MCP-4, IP-10, BDNF, Eotaxin-3, Eotaxin, and TARC. Probes may further include α1AT, VCAM-1, ICAM-1, HGF, and VEGF-A. Probes may also include those for components of the complement cascade, e.g., C1q, C3c and C3d. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

The panels or arrays of the invention may also include one or more probes capable of binding one or more of IL-2, IL-6, IL-8, IL-1B, and IFN-γ, wherein an altered plasma or serum concentration of one or more relative to a healthy control is indicative of seizure or a tendency to have seizure. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In still further embodiments, the polypeptide expression panel or arrays described herein may include one or more probes capable of binding IL-10, IL-12 p70, Fas, Fas-ligand, MCP-1, MDC, MIP-1β, GM-CSF, MCP-4, IP-10, BDNF, Eotaxin-3, Eotaxin, and TNF-α, wherein an altered plasma or serum concentration of one or more of IL-10, IL-12 p70, Fas, Fas-ligand, MCP-1, MDC, MIP-1β, GM-CSF, MCP-4, IP-10, BDNF, Eotaxin-3, Eotaxin, and/or TNF-α (relative to a healthy individual) indicates a tendency to have seizure. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In another embodiment, a method for predicting or detecting a seizure is provided, comprising contacting a blood plasma or blood serum sample obtained from a mammalian subject with a diagnostic reagent that can measure or detect the expression level of soluble ICAM-5 (sICAM-5) and contacting a blood plasma or blood serum sample obtained from a mammalian subject with a diagnostic reagent that can measure or detect the expression level of TARC, and contacting a blood plasma or blood serum sample obtained from a mammalian subject with a diagnostic reagent that can measure or detect the expression level of TNF-α, wherein a change in plasma or serum concentration of sICAM-5 relative to a healthy control and/or with a change plasma or serum concentration of TARC and a change plasma or serum concentration of TNF-α relative to a healthy control indicates a seizure having occurred or a tendency to have seizure. Individual measurements may be taken and analyzed individually or in any combination using linear or logarithmic units, or by using ratios of linear or logarithmic units. The reciprocals of ratios of linear or logarithmic units may also be used.

The method may also include contacting the blood plasma or blood serum sample with one or more diagnostic reagents that can measure or detect the expression level of IL-2, IL-6, IL-8, IL-1β, and/or IFN-γ, wherein altered plasma or serum concentration of one or more of IL-2, IL-6, IL-8, IL-1β, and IFN-γ relative to a healthy control indicates a tendency to have seizure. Still further, the method may include contacting the blood plasma or blood serum sample with a diagnostic reagent that can measure or detect the expression level of one or more diagnostic reagents that can measure or detect the expression level of IL-10, IL-12 p70, Fas, Fas-ligand, MCP-1, MDC, MIP-1β, GM-CSF, MCP-4, IP-10, BDNF, Eotaxin-3, Eotaxin, and/or TNF-α, wherein altered plasma or serum concentration of one or more of IL-10, IL-12 p70, Fas, Fas-ligand, MCP-1, MDC, MIP-1β, GM-CSF, MCP-4, IP-10, BDNF, Eotaxin-3, Eotaxin, and TNF-α relative to a healthy control indicates a seizure having occurred or a tendency to have a seizure. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In yet another embodiment, a method for assessing the effectiveness of a treatment of seizure or a disorder for which seizure is symptomatic is provided, the method including contacting a first blood plasma or blood serum sample obtained from a mammalian subject prior to treatment with one or more diagnostic reagents that can measure or detect the expression level of soluble ICAM-5 (sICAM-5) and/or TARC and/or TNF-α, and contacting a second blood plasma or blood serum sample obtained from a mammalian subject subsequent to treatment with a diagnostic reagent that can measure or detect the expression level of soluble ICAM-5 (sICAM-5) and/or TARC and/or TNF-α, wherein an altered plasma or serum concentration of sICAM-5 and/or a altered level of TARC in the second blood plasma or blood serum sample and/or a altered level of TNF-α in the third blood plasma or blood serum sample relative to the first blood plasma or blood serum sample indicates effectiveness in treatment of seizure or a disorder for which seizure is symptomatic. The method may further include contacting the first blood plasma or blood serum sample and the second blood plasma or blood serum sample with one or more diagnostic reagents that can measure or detect the expression level of IL-, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α, wherein an altered concentration of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α in the second blood plasma or blood serum sample relative to the first blood plasma or blood serum sample indicates effectiveness in treatment of seizure or a disorder for which seizure is symptomatic. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In still further embodiments, a method for determining whether or not one or more seizures are resultant from inflammation, comprising contacting a blood plasma or blood serum sample obtained from a mammalian subject with a diagnostic reagent that can measure or detect the expression level of soluble ICAM-5 (sICAM-5) and/or contacting a blood plasma or blood serum sample obtained from a mammalian subject with a diagnostic reagent that can measure or detect the expression level of TARC, wherein an altered plasma or serum concentration of sICAM-5 relative to a healthy control and/or an altered plasma or serum concentration of TARC indicates an inflammatory basis or component of seizure. The method may further include contacting the blood plasma or blood serum sample with one or more diagnostic reagents that can measure or detect the expression level of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α, wherein an altered concentration of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α in the blood plasma or blood serum sample indicates an inflammatory basis or component of seizure. Still additional markers that may be useful in the invention, and that may provide information on anti-inflammatory response, include, alone or in combination, IL-1 receptor antagonist, IL-4, IL-10, IL-11, IL-13, leukemia inhibitory factor, interferon-alpha, IL-6 and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In yet other embodiments, a method for determining whether or not seizure is likely to occur in a subject is provided, comprising contacting a blood plasma or blood serum sample obtained from a mammalian subject with a diagnostic reagent that can measure or detect the expression level of soluble ICAM-5 (sICAM-5) and/or contacting a blood plasma or blood serum sample obtained from a mammalian subject with a diagnostic reagent that can measure or detect the expression level of TARC, wherein a altered plasma or serum concentration of sICAM-5 relative to a healthy control and/or an altered plasma or serum concentration of TARC indicates a tendency to have seizure. The method may further include contacting the blood plasma or blood serum sample with one or more diagnostic reagents that can measure or detect the expression level of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α, wherein an altered concentration of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α in the blood plasma or blood serum sample indicates a tendency to have seizure. Individual measurements may be taken and analyzed individually or in any combination using linear or logarithmic units, or by using ratios of linear or logarithmic units. The reciprocals of ratios of linear or logarithmic units may also be used.

In yet other embodiments, a method for determining the whether or not seizure is likely to occur in a subject is provided, comprising contacting a blood plasma or blood serum sample obtained from a mammalian subject with a diagnostic reagent that can measure or detect the expression level of soluble ICAM-5 (sICAM-5) and/or contacting a blood plasma or blood serum sample obtained from a mammalian subject with a diagnostic reagent that can measure or detect the expression level of TNF-α, wherein a altered plasma or serum concentration of sICAM-5 relative to a healthy control and/or an altered plasma or serum concentration of TNF-α indicates a tendency to have seizure. The method may further include contacting the blood plasma or blood serum sample with one or more diagnostic reagents that can measure or detect the expression level of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α, wherein an altered concentration of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α in the blood plasma or blood serum sample indicates a tendency to have seizure. Individual measurements may be taken and analyzed individually or in any combination using linear or logarithmic units, or by using ratios of linear or logarithmic units. The reciprocals of ratios of linear or logarithmic units may also be used.

In yet other embodiments, a method for determining the whether or not seizure is likely to occur in a subject is provided, comprising contacting a blood plasma or blood serum sample obtained from a mammalian subject with a diagnostic reagent that can measure or detect the expression level of TARC and/or contacting a blood plasma or blood serum sample obtained from a mammalian subject with a diagnostic reagent that can measure or detect the expression level of TNF-α, wherein an altered plasma or serum concentration of TARC relative to a healthy control and/or an altered plasma or serum concentration of TNF-α indicates a tendency to have seizure. The method may further include contacting the blood plasma or blood serum sample with one or more diagnostic reagents that can measure or detect the expression level of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and/or TNF-α, wherein an altered concentration of IL-6, IL-8, IL-2, IL-1β, IFN-γ, IL-10, IL-12 p70, Fas, Fas-ligand, MCP-1, MDC, GM-CSF, MCP-4, IP-10, BDNF, Eotaxin-3, Eotaxin, and/or TNF-α in the blood plasma or blood serum sample indicates a tendency to have seizure. Individual measurements may be taken and analyzed individually or in any combination using linear or logarithmic units, or by using ratios of linear or logarithmic units. The reciprocals of ratios of linear or logarithmic units may also be used.

For any biomarker selected, individual measurements may be taken and analyzed individually or in any combination using linear or logarithmic units, or by using ratios of linear or logarithmic units. The reciprocals of ratios of linear or logarithmic units may also be used.

In further embodiments of the above, the seizure may be associated with a temporal lobe epilepsy. In a further embodiment, the temporal lobe epilepsy may be mesial temporal sclerosis (MTS). In other embodiments, the seizure may be associated with tuberous sclerosis complex (TSC).

In further embodiments, the seizure may be classified according to the: Operational Classification of Seizure Types by the International League Against Epilepsy, which is located at the following web address: www.ilae.org/visitors/centre/documents/ClassificationSeizureILAE-2016.pdf.

In still other specific further embodiments of the above, the seizure may be cryptogenic. In further embodiments, the seizure is not associated with immune response to a pathogen.

The embodiments, including the probes and panels/arrays of probes, described herein may be used to detect whether or not a seizure has (or is likely to have) occurred. They may also be used to predict the likelihood of further seizure. Additionally, they may be used to predict whether or not seizure is likely following a brain injury or head trauma. They are also useful in identifying whether or not a seizure is the result of an inflammatory process. Further, they may be used in assessing whether or not a treatment is effective.

By way of non-limiting example, the following polypeptide panels or arrays are embodiments of the application (the terms altered, elevated, and altered refer to the expression level in the epileptic patient versus that in a healthy subject):
  sICAM-5;
  TARC;
  TNF-α;
  sICAM-5, TARC;
  siCAM-5, TNF-α;
  TARC, TNF-α;
  siCAM-5, TARC, TNF-α.

Other polypeptide panels or arrays are embodiments of the application, and may include the above and additionally one or more of the following:
  IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin;
  IL-1 receptor antagonist, IL-4, IL-10, IL-11, IL-13, leukemia inhibitory factor, interferon-alpha, IL-6 and TGF-13 family members (TGF-β1 to -β5).

Samples may be obtained from patients by conventional techniques. These techniques may include those covered by an institutional review board (IRB) approved protocol, including blood, urine, saliva and CSF. In one embodiment, the samples are anticoagulated using sodium citrate. In a further embodiment, plasma is prepared by centrifuging samples, e.g., at 5,000 g (g =gravity) for 15 minutes at 4° C. Controls may also be purchased from commercial vendors.

Levels (concentrations) of the polypeptide to be quantified in plasma may be obtained by any of a number of methods known in the art, the particular procedure not being a limitation of the embodiments herein. For example, ELISA, Indirect ELISA, Sandwich ELISA, Competitive Elisa, and Multiple and Portable (M&P) ELISA may be used. Probes specific to the antigen (polypeptide or marker) to be detected may be obtained commercially or designed by techniques known in the art. In one embodiment for sICAM-5 detection, protein G affinity purified mouse monoclonal anti-human ICAM-5 antibody is used as the capture antibody. Single- and multi-probe kits are available from commercial suppliers, e.g., Meso Scale Discovery. These kits include the kits referenced in the Examples hereto. Individual measurements may be taken and analyzed individually or in any combination using linear or logarithmic units, or by using ratios of linear or logarithmic units. The reciprocals of ratios of linear or logarithmic units may also be used.

Also described herein are methods of treating or preventing seizure or a disorder for which seizure is symptomatic in a mammalian subject or patient, comprising delivery of sICAM-5. In a further embodiment, the mammal is a human. Also provided is use of sICAM-5 to treat or prevent seizure or a disorder for which seizure is symptomatic in a mammalian subject, and use in preparing a medicament therefor. Given that ICAM-5 is expressed on the surface of telencephalic neurons (i.e., is localized to the brain), treatment or prevention may be effected without undesired systemic effects.

Treatment or prevention may be made intravenous or via intra-cerebrospinal fluid (intra-CSF) by techniques known to one of skill in the art. Delivery may also be made by any other suitable means, including by intranasal delivery to the CSF with a suitable carrier or excipient.

Other Applications

In some embodiments of the invention, biomarkers and algorithms that form a blood-based diagnostic test, such as EvoScore, as described herein, can be leveraged for seizure prediction; anti-epileptic drug (AED) clinical trial eligibility, endpoints, and effectiveness; multiple diagnostic combinations including EEG, MRI, Genomics, Genetics and proteomics, companion diagnostics; and potential identification of inflammation based therapeutics and response. In some embodiments, the blood-based diagnostic test described herein may be used to determine absolute changes in biomarker levels in an event as well as relative changes in biomarkers in a patient over time. In some embodiments, the biomarkers and algorithms in the blood-based diagnostic test described herein in known epilepsy patients who are well-controlled with medications, may be used to prepare a corresponding score and a user may determine if the score correlates with AED responsiveness and, by extension, predict subsequent breakthrough seizures and medical intractability. Similarly, the blood-based diagnostic test described herein may be used to predict AED response in newly identified epilepsy patients to quickly assess therapeutic response. In medically refractory patients after epilepsy surgery, the blood-based diagnostic test described herein may, in some embodiments, be provided that is predictive of surgical success. In some embodiments, the blood-based diagnostic test described herein, can be used to assess patients at risk for seizures following, for example, head injury or stroke to determine if their risk of seizures is increased. Furthermore, there is an important potential use in AED clinical trials to ensure more robust enrollment criteria resulting in faster, smaller trials allowing new medicines to reach patients earlier. In some embodiments, the blood-based diagnostic test described herein can be used as a personalized medicine diagnostic, to allow treatment and tracking of seizures and epilepsy over time, at defined intervals, to establish individualized response to therapies, effectiveness, control, and prediction of future events in order to improve patient quality of life and reduce burden on the healthcare system. In certain embodiments, the foregoing blood-based diagnostic test of the invention is EvoScore.

Test Methods

Blood was collected from human neurology patients or normal controls into lavender-topped vacutainer blood collection tubes containing $K_2EDTA$ as an anticoagulant (BD Biosciences). The blood collection tubes were inverted eight times, and then placed on wet ice at 4° C. for 10-15 minutes before centrifuging. The blood was centrifuged at 1000 RCF for 10 minutes at 4° C. Plasma supernatant was aliquotted into sterile 2 ml microtubes (Sarstedt, Type I) and frozen at −70° C. to −80° C.

Levels of TNF-α, TARC and ICAM5 in human plasma were measured in a sandwich ELISA with electrochemiluminescent detection using custom triplex plates from Meso Scale Discovery (MSD) (Gaithersburg, Md.) and the MSD Sector Imager 2400. We purchased MULTI-SPOT 96-well Custom 4 Spot plates (TNF-α, TARC, ICAM5, BSA) MSD ELISA plates and TNF-α and TARC coating/capture antibodies from MSD. ICAM5 coating/capture antibodies were purchased from R&D Systems (MAB1950). For all incubation steps, plates were sealed with adhesive plate seals (Denville B1212-4S) and incubations were performed at room temperature (RT) with rotation (400rpm) on a microtiter plate shaker (Denville 210A #CO210). In all wash steps, wells were emptied and then washed three times with 175 µL of Phosphate Buffered Saline (PBS) (Denville CP4390-48) with 0.05% Tween-20 (Fisher BP 337-500) (PBST). All blood products and contaminated materials were decontaminated with a minimum final concentration of 10% bleach. Reverse pipetting was employed to avoid the production of bubbles throughout the assay.

To run samples, custom plates were removed from 4° C. and allowed to equilibrate to room temperature for 30 to 60 minutes. Unbound sites were blocked with 150 µl per well of blocking solution (10% Fetal Bovine Serum (FBS) (Mediatech 35-016-CV) in PBS, incubated for two hours, and then washed.

TNF-α and TARC protein standards were purchased from MSD, and recombinant human ICAM-5 protein standard was purchased from R&D Systems (1950-M5-050). Calibrator proteins were diluted in 25% Horse Plasma (Innovative Research IHR-N prepared with $K_2EDTA$ to coordinate with lavender-top tube content) in 5% FBS in PBS. Triplex standard curve starting concentrations for TNF-α and TARC were 2500 pg/ml, starting concentration for ICAM5 was 50,000 pg/ml, and this was diluted at 1:5. 100 µl of standard was plated in duplicate, including a protein-free duplicate well set. Human plasma samples were diluted 1:4 in 5% FBS in PBS to a final concentration of 25% sample, and 100 µl was plated. Standards and samples were incubated for three hours and plates were washed before addition of antibodies.

Biotinylated anti-human ICAM5 antibody was purchased from R&D systems (BAF1950). Streptavidin-SULFOTAG and SULFOTAG-labeled anti-human TNF-α and TARC antibodies were purchased from MSD. Primary antibodies were diluted to 1:50 and streptavidin-SULFOTAG was diluted 1:500 in 1% Bovine Serum Albumin (Fisher BP1605-100) in PBS. Primary antibodies and streptavidin-SULFOTAG were incubated in one step for 90 minutes. The specificity of the MSD assay allows for a single-step detection incubation as opposed to a two-step incubation. Plates were then washed before developing and reading.

4× MSD Read Buffer T was diluted to 2× with sterilized reverse-osmosis $H_2O$. Plates were developed by adding 150 µl of RT 2× Read Buffer T to each well, and then read immediately on the MSD Sector Imager 2400 coupled with the MSD Discovery Workbench 4.0 software. MSD Discovery Workbench 4.0 software was used to determine the protein concentrations of the plasma samples, and pg/ml results were multiplied by four to account for the 1:4 plasma sample dilution.

Patient Enrollment

A clinical trial was performed to determine whether EvoScore can be used effectively and accurately to diagnose patients with seizures, and to establish the threshold for diagnosis. All inpatient and outpatient subjects were 18 years of age or older and cognitively able to give informed consent. Subjects aged 18-20 provided assent, and a legally authorized representative gave consent on their behalf. There were no ethnic or gender limitations for these studies, and all eligible patients were recruited to ensure that there was no selection bias.

Inpatients admitted to an epilepsy monitoring unit (EMU) were invited to give a single sample of 15 ml of blood each morning and an additional 15 ml sample of blood following a seizure or seizure-like event. Inpatient subjects' EvoScore results were compared with all of their individual event diagnoses during their EMU stay, and their ultimate patient diagnosis at the conclusion of their EMU stay.

Outpatients were eligible to join the study only if they were attending their first visit at the outpatient neurology clinic for evaluation of their suspected seizures; these patients did not yet have a diagnosis of their events as either epileptic or non-epileptic. Outpatient subjects gave a single 15 mL sample of blood for research, and the study team collected all available clinical information relevant to their diagnostic workup for approximately 6 months after they joined the study. After six months, a team of independent neurologists evaluated their relevant medical history and "diagnosed" the subjects, and this diagnosis was compared to the EvoScore results to determine diagnostic accuracy (agreement among two epileptologists was sufficient).

Subjects 21 years of age and older who accompanied patients to epilepsy center appointments were considered to be normal controls and were eligible to join the study if they were cognitively able to provide informed consent, had not been diagnosed with epilepsy, and were not taking any anti-epileptic drugs for any reason. A total of 401 study subjects were enrolled overall. 240 outpatients, 131 inpatients, and an additional 30 controls were enrolled from both the inpatient EMU and the outpatient neurology clinic. For the inpatient and outpatient subjects, the average age was 36.5 (range 18-82) and 52% were female (n=209).

Explanation of Individual Event Diagnosis (IED) and Patient Diagnosis (PD)

Inpatients initiated and ended their stays in the EMU. Outpatients were recruited from a neurology outpatient clinic, but some returned for a stay in the EMU. For all patients that stayed in the EMU, EMU reports were examined and the time was recorded of any observed neurological event immediately prior to the blood draw. The description of the event was also recorded, and neurologists independently diagnosed each individual event (Individual Event Diagnosis). Events were characterized as Non-Epileptic events (IED0), Epileptic events (with a positive EEG) (IED1), Unclear diagnosis event (IED2), or no event recorded (when there was no record of any event in the EMU report during that EMU stay) (IED3). When there was not agreement on the event diagnosis, the EMU reports were consulted and a consensus was reached. If no consensus could be reached, the event was rated with an unclear diagnosis (IED2). Individual event diagnosis is considered evaluation of phasic changes. Individual event diagnosis can also be called event diagnosis.

The final overall patient diagnosis recorded in the "Epilepsy Diagnosis" section of the EMU report was used for each patient for the Patient Diagnosis (PD). Patients either received a diagnosis of Non-Epilepsy (PD0), Epilepsy (PD1), Epilepsy +Other Non-Epileptic condition PD2), or an Unclear diagnosis (PD3). Patient diagnosis is considered evaluation of tonic changes.

Predictive Models and Score

As used herein, a "predictive model," which term may be used synonymously herein with "multivariate model" or simply a "model," is a mathematical construct developed using a statistical algorithm or algorithms for classifying sets of data. Predictive models can provide an interpretation function; e.g., a predictive model can be created by utilizing one or more statistical algorithms or methods to transform a dataset of observed data into a meaningful determination of disease activity or the disease state of a subject. Algorithms developed herein, based upon concentrations and ratios of biomarkers, and or combined with patient demographic characteristics, identify the phasic and tonic changes (acute and chronic) associated with a seizure event. Individual measurements may be taken and analyzed individually or in any combination using linear or logarithmic units, or by using ratios of linear or logarithmic units. The reciprocals of ratios of linear or logarithmic units may also be used.

The predictive model can be used in all clinical settings for one or more of following purposes (a) ruling in or ruling out seizure; (c) assessing the patient quality of life by predicting when and if seizures will continue to occur; and (c) the ability of a therapeutic or therapeutic protocol to control the seizures over time.

As used herein, a "score" is a value or set of values selected so as to provide a quantitative measure of a variable or characteristic of a subject's condition, and/or discriminate, differentiate or otherwise characterize a subject's condition. The values(s) comprising the score can be based on, for example, a measured amount of one or more sample constituents obtained from the subject or from clinical parameters or from clinical assessments or any combination thereof. In certain embodiments the score can be derived from a single constituent parameter or assessment, while in other embodiments the score is derived from multiple constituents, parameters and/or assessments. The score can be based upon or derived from an interpretation function, e.g., an interpretation function derived from a particular predictive model using any of carious statistical algorithms known in the art. A "change in score" can refer to the absolute change in score, e.g., from one time point to the next, or the percent change in score, or the change in the score per unit of time. For example, a score referred to herein may be provided by a blood-based diagnostic test of the invention (e.g., EvoScore).

The score can be use to rate and/or measure the phasic and tonic changes, rule in or rule out an event, evaluate patient quality of life and therapeutic effectiveness, by providing numerically "quantitative" or high, medium or low "qualitative" or Positive or Negative "qualitative" or other form to convey results of phasic and/or tonic changes in the identification of seizure and epilepsy.

The predictive models and scores can be used in combination with any of the current standard diagnostic techniques, including EEG and MRI to develop an ultimate patient diagnosis. The predictive score would add improved accuracy in terms of sensitivity, specificity, positive predictive value and negative predictive value when combined with other standard diagnostic techniques.

Algorithm Objectives, Thresholds and Actionable Results

Scoring algorithms included in the blood-based diagnostic tests described herein (e.g., EvoScore) were developed by the following methodologies: (a) For individual event diagnosis of seizure or not: Classification Tree and Regression analysis and/or Multiple Logistic Regression which may include risk groups defined by the classification tree analysis; and (b) For patient diagnosis of epilepsy or not: Logistic regression and Multiple Logistic Regression including risk groups defined by classification tree analysis.

EvoScore algorithms and methodologies for both individual event diagnosis of seizure or not and patient diagnosis of epilepsy or not were determined to be a function of measurable changes of the concentration, natural logarithm scaled changes in the concentration, ratios of the biomarkers and ratios of the scaled concentrations of TARC, sICAM5 and TNF-α and can include patient physical characteristics, including age, sex and prescription information.

All of these methodologies and results yielded algorithms meeting diagnostic test clinical and market performance and accuracy objectives. The algorithms' predictive results are designed to maximize sensitivity and True Positives, and minimize False Negatives, and maximize accuracy and correctly classified. Specificity and True Negatives can also be maximized with minimal false positives.

Thresholds or quantitative boundaries can be set to both maximize individual diagnostic values and or optimize combinations of diagnostic values, including sensitivity, specificity, and positive and negative predicted value. Different embodiments of the algorithms can use different thresholds depending on the goals of the algorithm. Thresholds can ultimately determine how a score is interpreted as the individual test score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative." Ultimate selection of thresholds are driven by the maximization and/or optimization of one or more characteristics of diagnostic accuracy as desired for performance.

FIG. 1 defines the objectives of the algorithm and ultimate actionable results.

Combination Diagnostic and Therapeutic Approaches

To achieve the maximum therapeutic benefits for individual subjects, it is important to be able to specifically quantify and assess the subject's disease burden at any particular time, determine the effects of treatment on disease activity, and predict future outcomes. The embodiments of the present teachings identify multiple serum biomarkers for accurate clinical assessment of disease activity in subjects with acute and chronic disease.

Current therapeutic approaches for epilepsy, include and are not limited to therapeutically effective dose of an antiepileptic compound selected from the group consisting of phenytoin, fosphenytoin, midazolam, pregabalin, brivaracetam, peram panel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. New therapeutic approaches are currently in development and are applicable to diagnostic evaluation and can be combination diagnostic and therapeutic approaches.

In some embodiments, a blood-based diagnostic test of the invention (e.g., EvoScore) can evaluate known epilepsy patients who are well-controlled with medications to determine if the score correlates with AED responsiveness and by extension, if changes in EvoScore predict subsequent breakthrough seizures and medical intractability. In some embodiments, a blood-based diagnostic test of the invention (e.g., EvoScore) can predict AED response in newly identified epilepsy patients to quickly assess therapeutic response. In some embodiments, a blood-based diagnostic test of the invention (e.g., EvoScore) can be used to assess in medically refractory patients after epilepsy surgery to determine if the score can predict surgical success. In some embodiments, a blood-based diagnostic test of the invention (e.g., EvoScore) can be used to assess patients at risk for seizures following for example, head injury or stroke to determine if their risk of seizures is increased. In some embodiments, a blood-based diagnostic test of the invention (e.g., EvoScore) can be used as a personalized medicine diagnostic, to allow for the treatment and tracking of seizures and epilepsy over time, at defined intervals, to establish individualized response to therapies, effectiveness, control, and prediction of future events in order to improve patient quality of life and reduce burden on the healthcare system.

In some embodiments, a blood-based diagnostic test of the invention (e.g., EvoScore) can be used in combination with EEG, MRI and other diagnostic approaches described herein.

In other embodiments, EvoScore alone, or in combination with other biomarkers as described herein and/or other clinical tests, can be utilized in other neurological diseases/indications including migraine, traumatic brain injury, stroke, infections and immune response to a pathogen, autoimmune response, immune response, tumors and other neurological diseases/indications with an inflammation component and/or effect.

Kits

In an embodiment, the invention provides a diagnostic kit comprising a polypeptide expression panel or array. The kit may also be predictive, useful in determining imminent risk of seizure or recurrence of seizure, or in assessing recurrence risk. The kit may also contain a syringe and/or vile for drawing blood. The kit may contain one or more probes corresponding to the polypeptide markers of the panel or array. The kit may also contain an ELISA plate based on chemiluminest, luminist or equivalent technology. A multiple and portable (M&P) ELISA may also be provided as part of a kit of an embodiment. Still other suitable components will be known to one of skill in the art, and are encompassed hereby. Kits may include software, computers and instruments for presenting the diagnostic result.

Other aspects of the present invention provide a kit for the kit comprising: (a) assay (b) instructions (c) computer or computer system to perform a method of the present invention, or, in (d) other embodiments, an algorithm that forms part of a method of the present invention.

Other embodiments comprise biomarker detection reagents packaged together in the form of a kit for conducting any of the assays of the present teachings. In certain embodiments, the kits comprise oligonucleotides that specifically identify one of more biomarker nucleic acids based on homology and/or complimentary with biomarker nucleic acids. The oligonucleotide sequences may correspond to fragments of the biomarker nucleic acids. For example, the oligonucleotides can be more than: 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody, control formulations (positive and/or negative), and/or a detectable label. Instructions for carrying out the assay, including optionally instructions for generating a score can be included in the kit. The assay can be in the form of ELISA as known in the art.

Software, Instruments and Computers

The predictive models can be manually or automatically performed using software engineered for performing such a task. The analysis of concentrations of selected biomarkers may be performed manually or alternatively the analysis may be performed using software engineered for performing such a task. In preferred embodiments, an algorithm forms part of a predictive method of the present invention analyzes the concentrations of the selected biomarkers to present the diagnostic result or score. The algorithm may be performed manually or automatically via software engineered. The software engineered may be part of the instrument reading the concentrations of the selected biomarkers or may be part of an external computer. In other embodiments, the aforementioned software is loaded onto a computer. The computer also interfaces with the instrument inputs data directly from the instrument either manually or automatically. Individual measurements may be taken and analyzed individually or in any combination using linear or logarithmic units, or by using ratios of linear or logarithmic units, with and/or without patient demographic characteristics. The reciprocals of ratios of linear or logarithmic units may also be used. In some embodiments, the computer belongs to the end user, while in other embodiments, the computer or processor is provided as part of the kit. In preferred embodiments, the software engineered directs the computer to (a) access a file containing data from the instrument and (b) analyze these data using an algorithm of the invention. In other embodiments, the software engineered presents the results in a user-friendly format for interpreting the diagnostic results.

In some embodiments, methods and systems of the invention, can be embodied as a computer implemented process or processes for performing such computer-implemented process or processes, and can also be embodied in the form of a tangible storage medium (i.e., non-transitory computer readable medium) containing a computer program or other machine-readable instructions (herein "computer program"), wherein when the computer program is loaded into a computer or other processor (herein "computer") and/or is executed by the computer, the computer becomes an apparatus for practicing the process or processes. Storage media for containing such computer program include, for example, floppy disks and diskettes, compact disk (CD)-ROMs (whether or not writeable), DVD digital disks, RAM and ROM memories, computer hard drives and back-up drives, external hard drives, solid state drives, "thumb" drives, and any other storage medium readable by a computer. The process or processes can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the process or processes. The process or processes may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation.

EXAMPLES

Reference is now made to the following examples, which, together with the above descriptions, illustrate certain embodiments of the invention in a non-limiting fashion. These examples are provided for the purpose of illustration only and the disclosure encompassed herein should in no way be construed as being limited to these examples, but rather should be construed to encompass any and all variations which become evident as a result of the teachings provided herein.

Example 1

Patient Demographics and Biomarker Data: Inpatients, Outpatients and Normal Controls Inpatient, outpatient and normal controls are shown in Table 1. Biomarkers alone including TARC and sICAM5, and the ratio of biomarkers TNFα/TARC and TNFα/sICAM5 were demonstrated to have statistically significant differences ($p<0.05$) between Normal Controls and Event Diagnosis, between Normal Controls and Patient Diagnosis 1, and between Normal Controls and Patient Diagnosis 1 & 2. These biomarkers and ratios of biomarkers can be used alone or in combination for the determination of seizure or not and epilepsy or not.

TABLE 1

Patient Demographics and Characteristics

| Variable | Patient Diagnosis 1 (N = 83) | Patient Diagnosis 1 & 2 (N = 99) | Event Diagnosis (N = 28) | Normal Controls (N = 29) |
|---|---|---|---|---|
| Age | 45.3 | 45.3 | 47.4 | 45.6 |
| 18-30 | 19.3% | 19.2% | 10.7% | 20.7% |
| 31-40 | 19.3% | 20.2% | 17.9% | 10.3% |
| 41-50 | 30.1% | 28.3% | 35.7% | 20.7% |
| 51+ | 31.3% | 32.3% | 35.7% | 48.3% |
| Sex | | | | |
| Male | 27.7% | 28.3% | 17.9% | 31.0% |
| Female | 72.3% | 71.7% | 82.1% | 69.0% |
| Labs | | | | |
| TNFalpha | 79.7 | 79.7 | 83.2 | 80.0 |
| TARC | 636.9 | 635.7 | 649.2 | 511.9 |
| sICAM5 | 18,236.0 | 17,588.3 | 19,460.7 | 14,680.8 |
| Ratios | | | | |
| TNF:TARC | 0.126 | 0.127 | 0.130 | 0.159 |
| TNF:sICAM5 | 0.0045 | 0.0046 | 0.0044 | 0.0054 |
| TARC:sICAM5 | 0.0371 | 0.0386 | 0.0355 | 0.0346 |

TABLE 1-continued

Patient Demographics and Characteristics

All Outpatients

| Variable | No Epilepsy (N = 63) | Epilepsy (N = 214) | All (N = 277) |
|---|---|---|---|
| Age | 44.0 | 37.0 | 38.6 |
| 18-30 | 28.6% | 45.3% | 41.5% |
| 31-40 | 14.3% | 16.4% | 15.9% |
| 41-50 | 23.8% | 16.8% | 18.4% |
| 51+ | 33.3% | 21.5% | 24.2% |
| Sex | | | |
| Male | 39.7% | 52.3% | 49.5% |
| Female | 60.3% | 47.7% | 50.5% |
| Labs | | | |
| TNFalpha | 113.0 | 115.2 | 114.7 |
| TARC | 707.2 | 800.0 | 778.9 |
| sICAM5 | 19,723.1 | 21,426.6 | 21,039.1 |
| TNF:TARC | 0.156 | 0.141 | 0.145 |

Outpatients with Clear Diagnosis

| Variable | No Epilepsy (N = 8) | Epilepsy (N = 127) | All (N = 135) |
|---|---|---|---|
| Age | 55.4 | 35.8 | 37.0 |
| 18-30 | 25.0% | 48.8% | 47.4% |
| 31-40 | 12.5% | 13.4% | 13.3% |
| 41-50 | 12.5% | 16.5% | 16.3% |
| 51+ | 50.0% | 21.3% | 23.0% |
| Sex | | | |
| Male | 50.0% | 53.5% | 53.3% |
| Female | 50.0% | 46.5% | 46.7% |
| Labs | | | |
| TNFalpha | 70.6 | 123.4 | 120.3 |
| TARC | 528.9 | 849.6 | 830.6 |
| sICAM5 | 13,091.4 | 22,347.0 | 21,798.5 |
| TNF:TARC | 0.137 | 0.142 | 0.142 |

Example 2

Event Diagnosis 24 Hours By Logistic Regression

Logistic Regression Model results may be used to classify events as either seizure/epileptic or no event. The data contains samples collected within 24 hours of an event. EvoScore algorithms were determined to be a function of measurable changes of the concentration for TARC, sICAM5 and TNF-α and patient physical characteristics, including age and sex.

Figure 3:
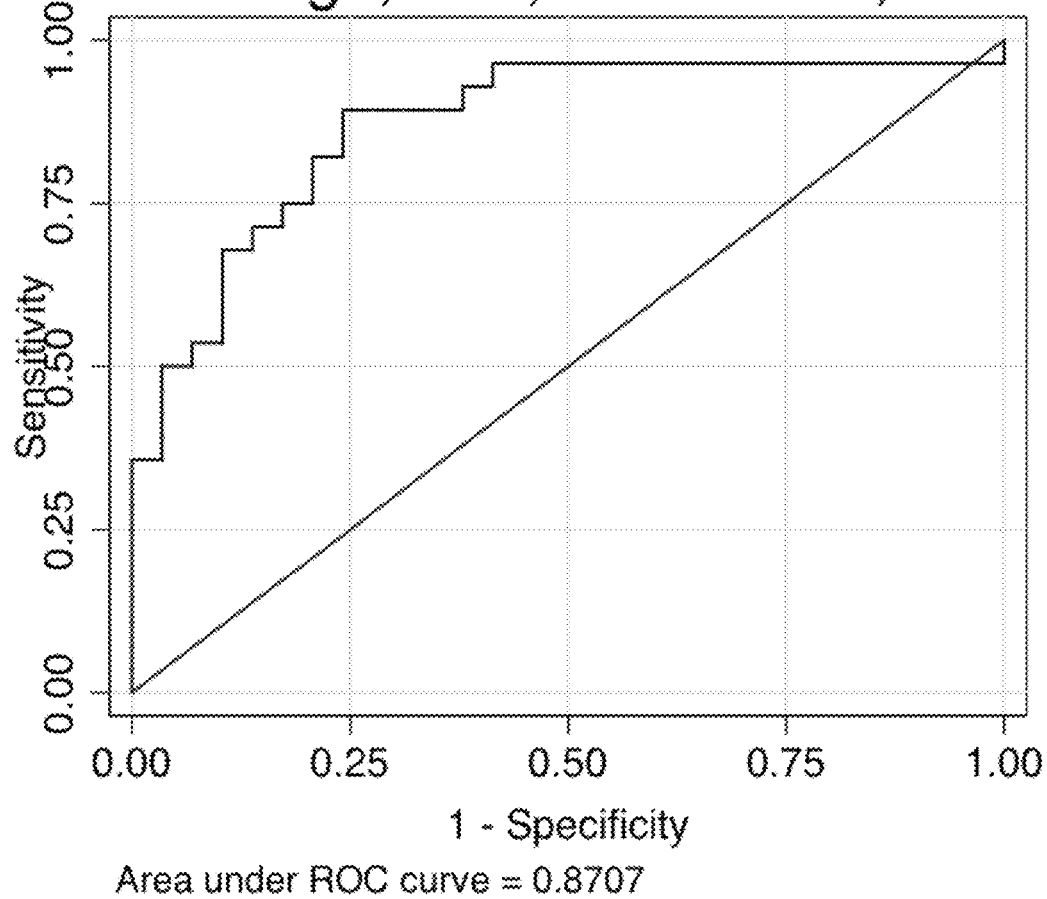
FIG. 3 illustrates the ROC curve obtained from modeling individual event diagnosis (24 hours) by logistic regression.

EvoScore demonstrated a Receiver Operating Characteristic (ROC) AUC of 0.8707 with 95% confidence interval of 0.7739 to 0.9675, Diagnostic Sensitivity of 89.3% (designed to maximize), Specificity of 75.9%, Positive Predictive Value of 78.1%, Negative Predictive Value of 88% and Accuracy of 82.5% (designed to maximize) for Patients with blood drawn within 24 hours of event when comparing patients with phasic and measureable changes for seizures versus normal controls. The results are summarized in TABLE 2 and FIG. 3.

TABLE 2

Results of event diagnosis (24 hours) by Logistic Regression.

| Variable | Coefficient | 95% Confidence Lower | 95% Confidence Upper | P-value |
|---|---|---|---|---|
| Labs | | | | |
| TNF:TARC | −35.81 | −58.21 | −13.41 | 0.002 |
| sICAM5 | 0.00014 | 0.00002 | 0.00025 | 0.018 |
| Sex | | | | |
| Male | REFERENCE | | | |
| Female | 0.829 | −0.720 | 2.379 | 0.294 |
| Age | | | | |
| 18-30 | REFERENCE | | | |
| 31-40 | 1.293 | −1.317 | 3.903 | 0.332 |
| 41-50 | 0.883 | −1.434 | 3.200 | 0.455 |
| 51+ | −0.021 | −2.306 | 2.264 | 0.986 |
| Constant | 1.729 | −2.553 | 6.011 | 0.429 |
| AROC | 87.07% | 0.7739 | 0.9675 | — |

$$EvoScore = \frac{e^{\phi}}{1 + e^{\phi}} \times 100$$

where
$\phi = 1.729 + 1.293 \times age3140 + 0.883 \times age4150 - 0.021 \times age51plus + 0.829 \times female - 35.81 \times TNF:TARC + 0.00014 \times sICAM5$ Max Correctly Classified

| Test Result | Patient Diagnosis + | Patient Diagnosis − |
|---|---|---|
| + | 25 | 7 |
| − | 3 | 22 |

| | |
|---|---|
| Sensitivity | 89.3% |
| Specificity | 75.9% |
| PPV | 78.1% |
| NPV | 88.0% |
| Accuracy | 82.5% |

Max Sum of Sensitivity and Specificity

| Test Result | Patient Diagnosis + | Patient Diagnosis − |
|---|---|---|
| + | 25 | 7 |
| − | 3 | 22 |

| | |
|---|---|
| Sensitivity | 89.3% |
| Specificity | 75.9% |
| PPV | 78.1% |
| NPV | 88.0% |
| Accuracy | 82.5% |

Example 3

Patient Studies: Event Diagnosis within 72 Hours By Logistic Regression

Multivariate Logistic Regression Model results may be used classify events as either seizure/epileptic or no event. The data contains samples collected within 72 hours of an event. EvoScore algorithms were determined to be a function of measurable changes of the concentration for TARC, sICAM5 and TNF-α and patient physical characteristics, including age and sex.

EvoScore demonstrated a ROC AUC of 0.8452 with 95% confidence interval of 0.7552 to 0.9353, Diagnostic Sensitivity of 84.4% (designed to maximize), Specificity of 72.4%, Positive Predictive Value of 82.6%, Negative Predictive Value of 75% and Accuracy of 79.7% (designed to maximize) for Patients with blood drawn within 72 hours of event when comparing patients with phasic and measureable changes for seizures versus normal controls. Results are summarized in Table 3.

TABLE 3

Results of event diagnosis (24 hours) by Logistic Regression.

| Variable | Coefficient | 95% Confidence | | P-value |
|---|---|---|---|---|
| | | Lower | Upper | |
| Labs | | | | |
| TNF:TARC | −36.01 | −55.34 | −16.68 | 0.000 |
| sICAM5 | 0.00010 | 0.00000 | 0.00020 | 0.040 |
| Sex | | | | |
| Male | REFERENCE | | | |
| Female | 0.618 | −0.747 | 1.983 | 0.375 |
| Age | | | | |
| 18-30 | REFERENCE | | | |
| 31-40 | 1.153 | −0.868 | 3.173 | 0.264 |
| 41-50 | 0.209 | −1.686 | 2.104 | 0.829 |
| 51+ | −0.950 | −2.692 | 0.792 | 0.285 |
| Constant | 3.605 | 0.213 | 6.997 | 0.037 |
| AROC | 84.52% | 0.7552 | 0.9353 | — |

Example 4

Patient Diagnosis 24 Hours By Logistic Regression

Logistic regression model results may be used to classify patients as either seizure/epileptic or normal including data from epilepsy, epilepsy plus other causes and normal controls. The data contains samples collected within 24 hours of an event. EvoScore algorithms were determined to be a function of measurable changes of the concentration for TARC, sICAM5 and TNF-α and patient physical characteristics, including age and sex.

Figure 4:
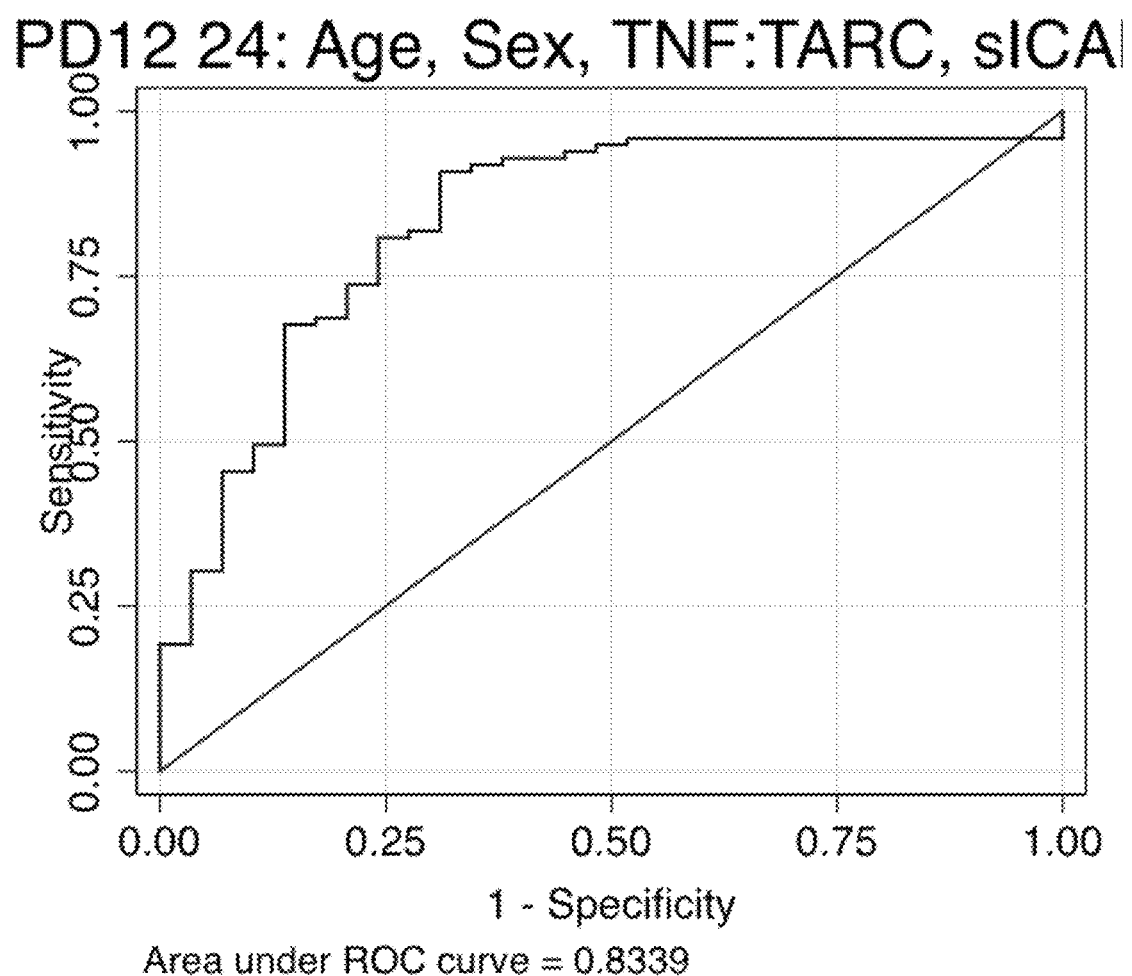
FIG. 4 illustrates the ROC curve obtained from modeling patient diagnosis (24 hours) by logistic regression.

EvoScore demonstrated a ROC AUC of 0.8339, with 95% confidence interval of 0.7456 to 0.9221, with Diagnostic Sensitivity of 90.9% (designed to maximize), Specificity of 69%, Positive Predictive Value of 90.9%, Negative Predictive Value of 69% and Accuracy of 85.9% (designed to maximize) for Patients with blood drawn within 24 hours of event when comparing patients with tonic and measureable changes for seizures and epilepsy versus normal controls. The results are summarized in TABLE 4 and FIG. 4.

TABLE 4

Results of patient diagnosis (24 hours) by multivarient logistic analysis.

| Variable | Coefficient | 95% Confidence | | P-value |
|---|---|---|---|---|
| | | Lower | Upper | |
| Labs | | | | |
| TNF:TARC | 33.67 | 49.59 | −17.76 | 0.000 |
| sICAM5 | 0.00012 | 0.00003 | 0.00022 | 0.009 |
| Sex | | | | |
| Male | REFERENCE | | | |
| Female | 0.245 | −0.813 | 1.304 | 0.650 |

TABLE 4-continued

Results of patient diagnosis (24 hours) by multivarient logistic analysis.

| Age | | | | |
|---|---|---|---|---|
| 18-30 | REFERENCE | | | |
| 31-40 | −0.423 | −2.195 | 1.349 | 0.640 |
| 41-50 | −0.550 | −2.165 | 1.066 | 0.505 |
| 51+ | −1.126 | −2.494 | 0.243 | 0.107 |
| Constant | 4.503 | 1.710 | 7.295 | 0.002 |
| AROC | 83.39% | 0.7456 | 0.9221 | — |

$$EvoScore = \frac{e^\phi}{1+e^\phi} \times 100$$

where
$\phi = 4.503 - 0.423 \times age3140 - 0.55 \times age4150 - 1.126 \times age51plus + 0.245 \times female - 33.67 \times TNF:TARC + 0.00012 \times sICAM5$ Max Correctly Classified

| Test | Patient Diagnosis | |
|---|---|---|
| Result | + | − |
| + | 92 | 11 |
| − | 7 | 18 |

| | |
|---|---|
| Sensitivity | 92.9% |
| Specificity | 62.1% |
| PPV | 89.3% |
| NPV | 72.0% |
| Accuracy | 85.9% |

Max Sum of Sensitivity and Specificity

| Test | Patient Diagnosis | |
|---|---|---|
| Result | + | − |
| + | 90 | 9 |
| − | 9 | 20 |

| | |
|---|---|
| Sensitivity | 90.9% |
| Specificity | 69.0% |
| PPV | 90.9% |
| NPV | 69.0% |
| Accuracy | 85.9% |

Example 5

Patient Diagnosis 24 Hours By Logistic Regression

Multivariate Logistic regression model results may be used to classify patients as either seizure/epileptic or normal including data from epilepsy and normal controls. The data contains samples collected within 24 hours of an event. EvoScore algorithms were determined to be a function of measurable changes of the concentration for TARC, sICAM5 and TNF-α and patient physical characteristics, including age and sex.

Figure 5:
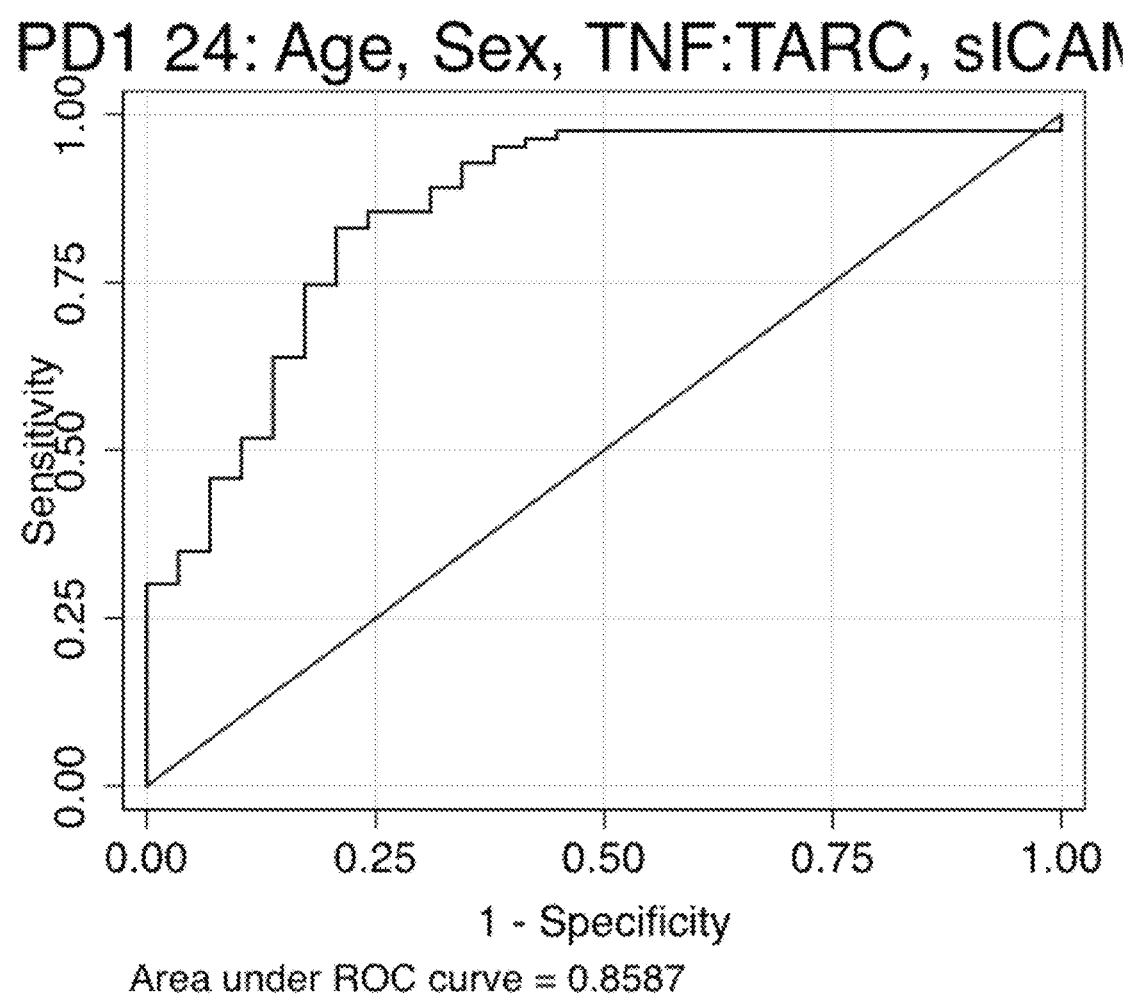
FIG. 5 illustrates the ROC curve obtained from modeling patient diagnosis (24 hours) by logistic regression.

EvoScore demonstrated a ROC AUC of 0.8587, with 95% confidence interval of 0.7754 to 0.9421%, with Diagnostic Sensitivity of 95.2% (designed to maximize), Specificity of 62.1%, Positive Predictive Value of 87.8%, Negative Predictive Value of 81.8% and Accuracy of 86.6% (designed to maximize) for Patients with blood drawn within 24 hours of event when comparing patients with tonic and measureable changes for seizures and epilepsy versus normal controls. The results are summarized in TABLE 5 and FIG. 5.

TABLE 5

Results of patient diagnosis (24 hours) by multivarient logistic analysis.

| Variable | Coefficient | 95% Confidence | | P-value |
|---|---|---|---|---|
| | | Lower | Upper | |
| Labs | | | | |
| TNF:TARC | −42.49 | −61.46 | −23.52 | 0.000 |
| sICAM5 | 0.00016 | 0.00005 | 0.00026 | 0.003 |
| Sex | | | | |
| Male | REFERENCE | | | |
| Female | 0.173 | −0.982 | 1.327 | 0.770 |
| Age | | | | |
| 18-30 | REFERENCE | | | |
| 31-40 | −0.007 | −1.792 | 1.779 | 0.994 |
| 41-50 | −0.164 | −1.870 | 1.542 | 0.851 |
| 51+ | −0.874 | −2.284 | 0.536 | 0.224 |
| Constant | 4.781 | 1.839 | 7.723 | 0.001 |
| AROC | 85.87% | 0.7754 | 0.9421 | — |

$$EvoScore = \frac{e^\phi}{1 + e^\phi} \times 100$$

where $\phi$ = 4.781 −0.007 × age3140 − 0.164 × age4150 − 0.874 × age51plus + 0.173 × female − 42.49 × TNF:TARC + 0.00016 × sICAM5

| Max Correctly Classified | | |
|---|---|---|
| Test | Patient Diagnosis | |
| Result | + | − |
| + | 79 | 11 |
| − | 4 | 18 |
| Sensitivity | 95.2% | |
| Specificity | 62.1% | |
| PPV | 87.8% | |
| NPV | 81.8% | |
| Accuracy | 86.6% | |

| Max Sum of Sensitivity and Specificity | | |
|---|---|---|
| Test | Patient Diagnosis | |
| Result | + | − |
| + | 69 | 6 |
| − | 14 | 23 |
| Sensitivity | 83.1% | |
| Specificity | 79.3% | |
| PPV | 92.0% | |
| NPV | 62.2% | |
| Accuracy | 82.1% | |

Example 6

Outpatient Analysis by Logistic Regression

For outpatients, an independent panel's diagnosis based on review of the six months of clinical care data was collected subsequent to EvoScore sampling and calculation was performed. Three independent board certified epileptologists were retained to review the diagnostic evaluations at the EMU and to confirm the diagnosis of seizure. The panel of epileptologists provided their best estimate of likely epileptic or likely non-epileptic events for this analysis, and agreement among two members of the panel will be sufficient and considered a consensus or agreed diagnosis.

For outpatients for whom our panel of at least 2 out of 3 independent reviewers agreed on a diagnosis, EvoScore accurately diagnosed 80-91% of outpatients as epileptic—where a clear epilepsy diagnosis was given; when applied to all-corners, including outpatients for whom there was minimal data and "unclear" epilepsy or normal, EvoScore agreed with the reviewers' consensus in diagnosing epilepsy in 82-83% of cases. This demonstrated that the test and predictive algorithms, along with in-patient data, work in all clinical settings.

Example 7

Event Diagnosis within 24 hours By Classification Tree Analysis

A classification and regression tree algorithm was used to stratify patient samples and control samples, and in turn, provides predictive values if an event of unknow origin was a seizure or an event of alternate origin. The classification tree could be constructed using either information gain (entropy) or best fit (gini impurity). The data contains samples collected within 24 hours of an event.

Figure 6:
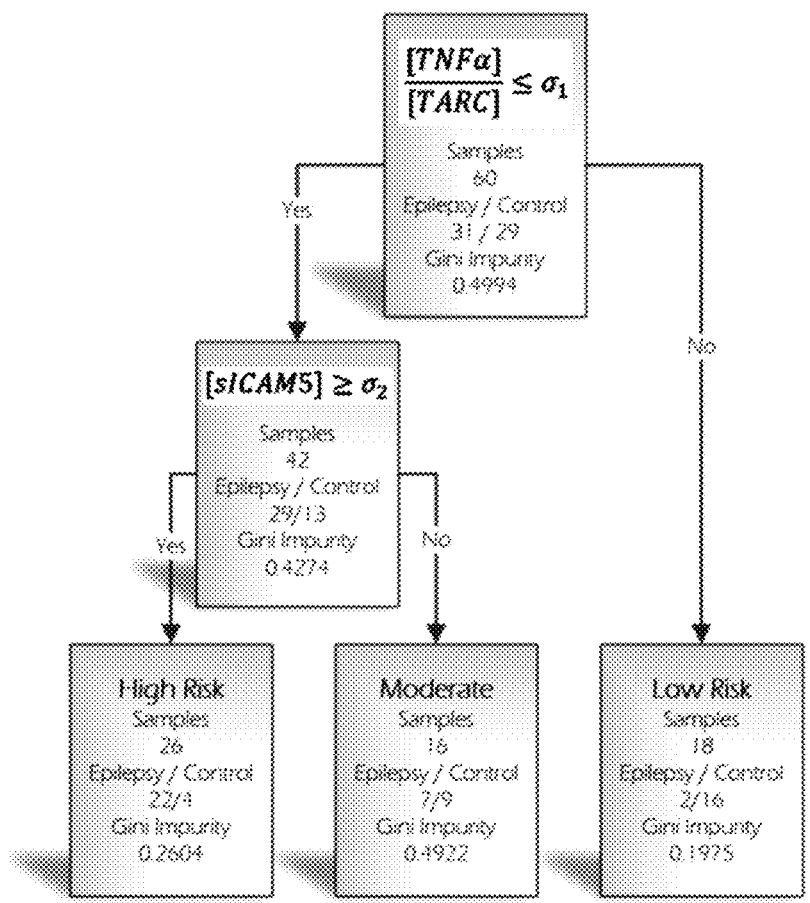
FIG. 6. Illustrates the performance of a classification tree algorithm to correctly stratify seizure events from control samples using a classification and regression tree algorithm.

Using a gini impurity cutoff of 0.2 and a maximum of two levels of classification tree depth the classification tree the classification tree correctly identified 26 samples as a high risk of having had a seizure, 16 samples as inconclusive (classified as Moderate risk in the figure) and 18 samples as not being a seizure event. Of the 26 samples identified as being a seizure event 84.6% were correctly classified. Correspondingly, 88.9% of the 18 non-seizure events were correctly identified. The classification tree is shown in FIG. 6.

Example 8

Event Diagnosis 24 Hours By Multiple Logistic Regression Including Risk Groups Defined vy Classification Tree Analysis Multiple Logistic Regression Model including risk groups defined by classification tree analysis. Results to Classify Events as Either Seizure/Epileptic or No Event. The data contains samples collected within 24 hours of an event. EvoScore algorithms were determined to be a function of measurable changes of the concentration for TARC, sICAM5 and TNF-α.

Figure 7:
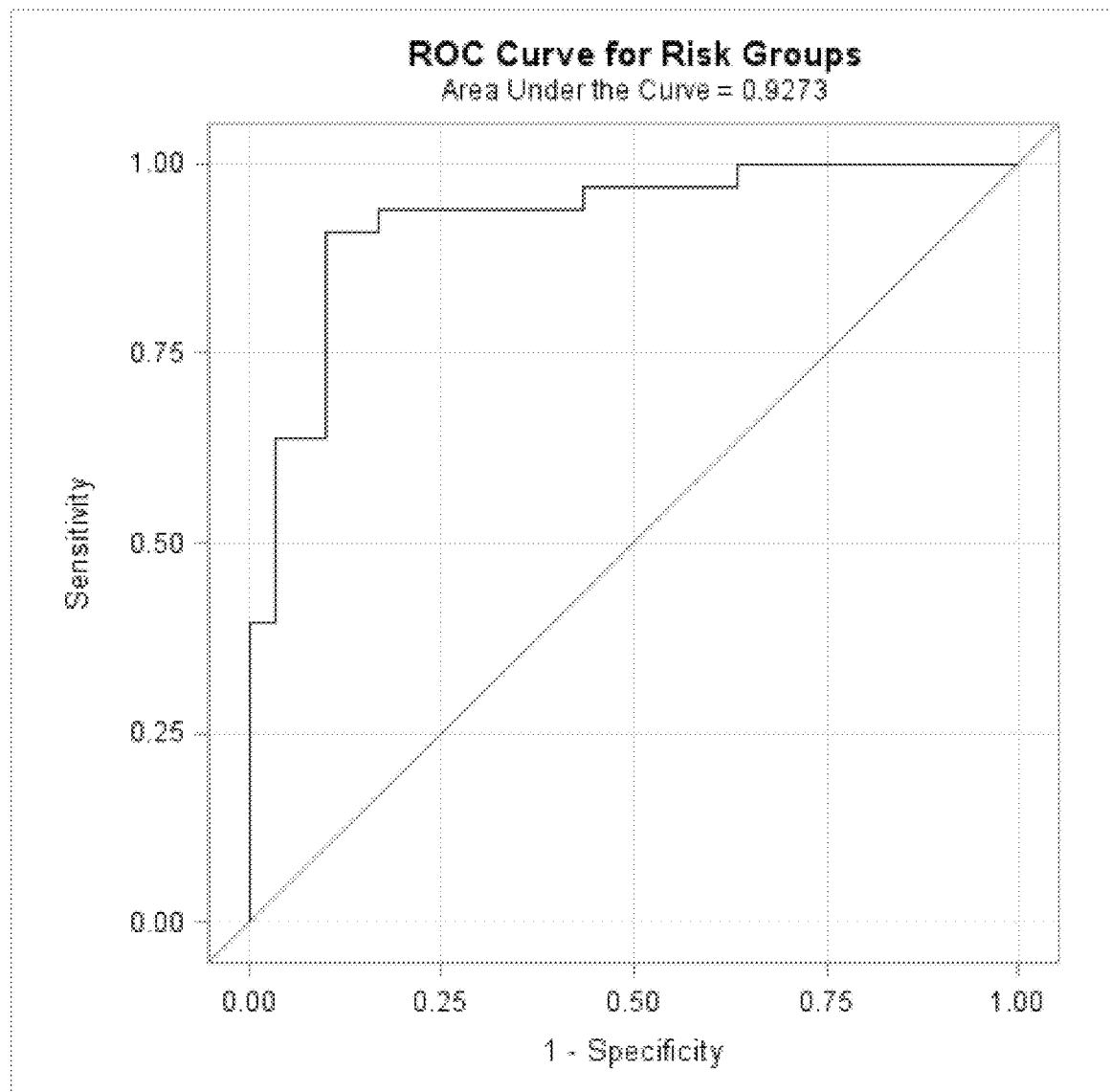
FIG. 7 illustrates the ROC curve obtained from modeling individual event diagnosis (24 hours) by Multiple Logistic Regression including risk groups defined by classification tree analysis.

EvoScore demonstrated a ROC AUC of 0.9273 with 95% confidence interval of 0.862 to 0.993, Diagnostic Sensitivity of 93.9% (designed to maximize), Specificity of 83.3%, Positive Predictive Value of 86.1%, Negative Predictive Value of 92.6% for Patients with blood drawn within 24 hours of event when comparing patients with phasic and measureable changes for seizures versus normal controls. The results are summarized in TABLE 6 and FIG. 7.

TABLE 6

Results of event diagnosis (24 hours).

| | P-value | AUROC | 95% CI |
|---|---|---|---|
| Tree Risk Groups + Biomarkers + Interactions | | 0.927 | 0.862, 0.993 |
| High Risk vs. Low Risk | 0.0195 | | |
| Moderate Risk vs. Low Risk | 0.1645 | | |
| Log sICAM-5 | 0.2021 | | |
| Log TARC | 0.0S68 | | |
| Log TNFa | 0.0369 | | |
| TNFa/sICAM-5 | 0.0076 | | |

TABLE 6-continued

Results of event diagnosis (24 hours).

| | |
|---|---|
| Log SICAM-5 * Log TNFa | 0.0527 |
| Log TARC * Log TNFa | 0.0586 |

Model using Predicted Probability of 0.5

| | Model Data | | |
|---|---|---|---|
| | True Positive | True Negative | |
| Predicted Positive | 31 | 5 | PPV = 86.1 |
| Predicted Negative | 2 | 25 | NPV = 92.6 |
| | Sensitivity = 93.9 | Specificity = 83.3 | |

| Model Parameters | Coefficient |
|---|---|
| Intercept | 218.8 |
| High Risk vs. Low Risk | 5.8459 |
| Moderate Risk vs. Low Risk | 2.9844 |
| Log SICAM-5 | −51.9285 |
| Log TARC | 65.8279 |
| Log TNFa | −150.6 |
| TNFa/SICAM-5 | 8207.5 |
| Log SICAM-5 * Log TNFa | 21.1553 |
| Log TARC * Log TNFa | −15.0138 |

EvoScore = $1/(1 + e^{\phi}) * 100$
Where
$\phi = 218.8 + 5.8459$(high risk group indicator) + 2.9844 (moderate risk group indicator) − 51.9285log(siCAM5) + 65.8279log(TARC) − 150.6log(TNPa) + $8207.5 \left(\frac{TNF_a}{sICAM5}\right) + 21.1553(\log(sICAM5) * \log(TNFa)) - 15.0138(\log(TARC) * \log(TNFa))$

Example 9

Event Diagnosis at All Times by Multiple Logistic Regression Including Risk Groups Defined by Classification Tree Analysis Multiple Logistic Regression Model including risk groups defined by classification tree analysis. Results to Classify Events as Either Seizure/Epileptic or No Event. The data contains samples collected at all times after an event. EvoScore algorithms were determined to be a function of measurable changes of the concentration for TARC, sICAM5 and TNF-α.

Figure 8:
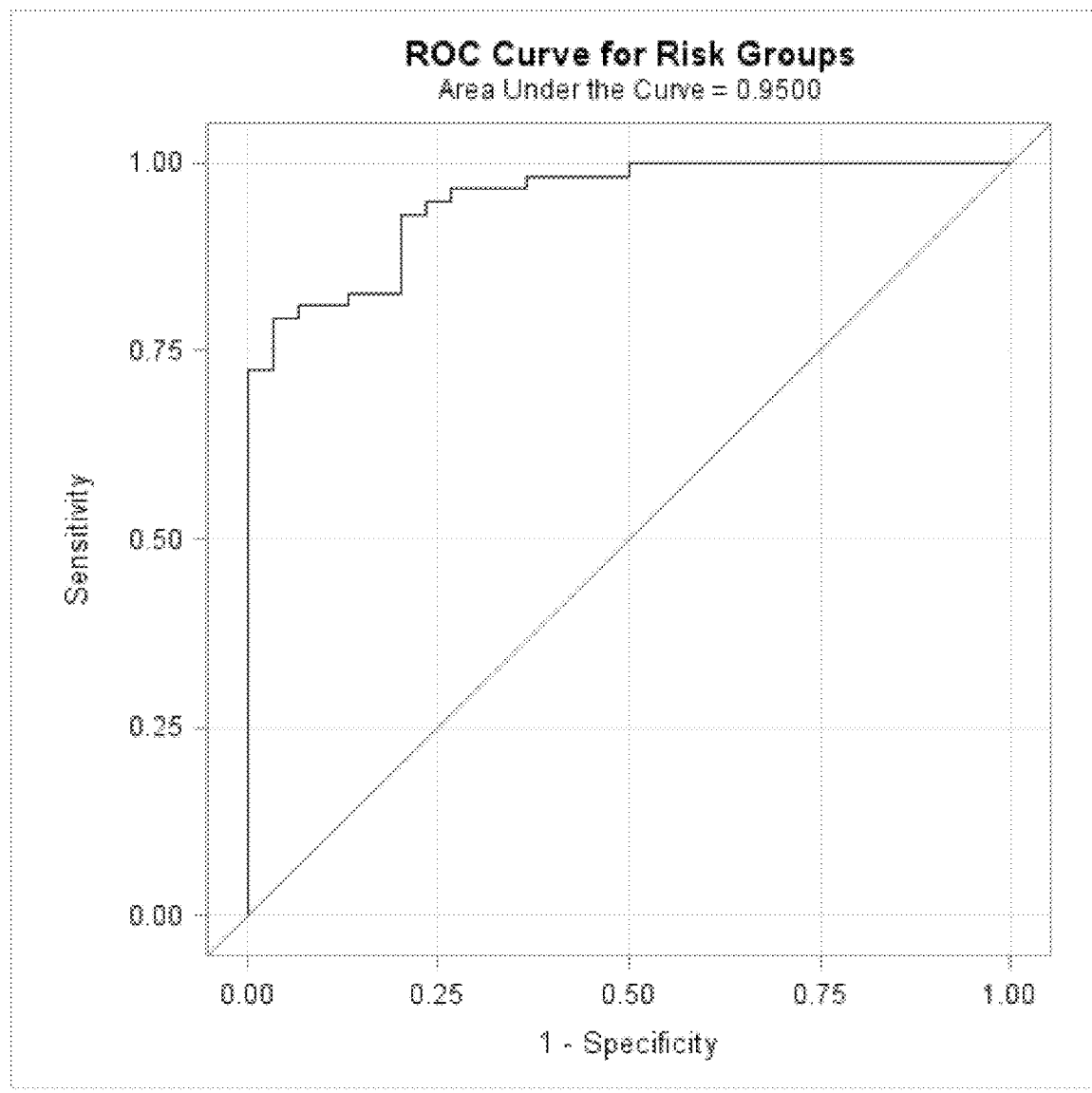
FIG. 8 illustrates the ROC curve obtained from modeling individual event diagnosis (all hours) by Multiple Logistic Regression including risk groups defined by classification tree analysis.

EvoScore demonstrated a ROC AUC of 0.9500 with 95% confidence interval of 0.911 to 0.990, Diagnostic Sensitivity of 93.1% (designed to maximize), Specificity of 73.3%, Positive Predictive Value of 87.1%, Negative Predictive Value of 84.6% and Accuracy of 86.4% (designed to maximize) for Patients with blood drawn at all times after event when comparing patients with phasic and measureable changes for seizures versus normal controls. Results are summarized in Table 7 and FIG. 8.

TABLE 7

Results of event diagnosis all times

| | P-value | AUROC | 95% CI |
|---|---|---|---|
| Tree Risk Groups + Biomarkers + Interactions | | 0.950 | 0.911, 0.990 |
| High Risk vs. Low Risk | | | |
| Log SICAM-5 | 0.0968 | | |
| Log TARC | 0.0105 | | |
| Log TNFa | 0.0035 | | |
| TNFa/SICAM-5 | 0.0038 | | |

TABLE 7-continued

| | | |
|---|---|---|
| TARC/SICAM-5 | 0.0396 | |
| Log TARC * Log TNFa | 0.0017 | |
| Log TARC* Log TNFa | 0.0017 | |

Model using Predicted Probability of 0.52

| | Model Data | | |
|---|---|---|---|
| | True Positive | True Negative | |
| Predicted Positive | 56 | 8 | PPV = 87.5 |
| Predicted Negative | 2 | 22 | NPV = 91.7 |
| | Sensitivity = 96.6 | Specificity = 73.3 | |

| Model Parameters | Coefficient |
|---|---|
| Intercept | −15.0645 |
| High Risk vs. Low Risk | 8.8955 |
| Log SICAM-5 | −53.1801 |
| Log TARC | 96.419 |
| Log TNFa | −178.1 |
| TNFa/SICAM-5 | 9758.9 |
| TARC/SICAM-5 | 1405.1 |
| Log TARC * Log TNFa | −36.6146 |
| Log SICAM-5 * Log TNFa | 37.968 |

Example 10

Patient diagnosis 24 hours by Multiple Logistic Regression Including Risk Groups Defined by Classification Tree Analysis Multiple Logistic regression model including risk groups defined by classification tree analysis. Results to classify patients as either seizure/epileptic or normal including data from epilepsy, epilepsy plus other causes and normal controls. The data contains samples collected within 24 hours of an event. EvoScore algorithms were determined to be a function of measurable changes of the concentration for TARC, sICAM5 and TNF-α.

Figure 9:
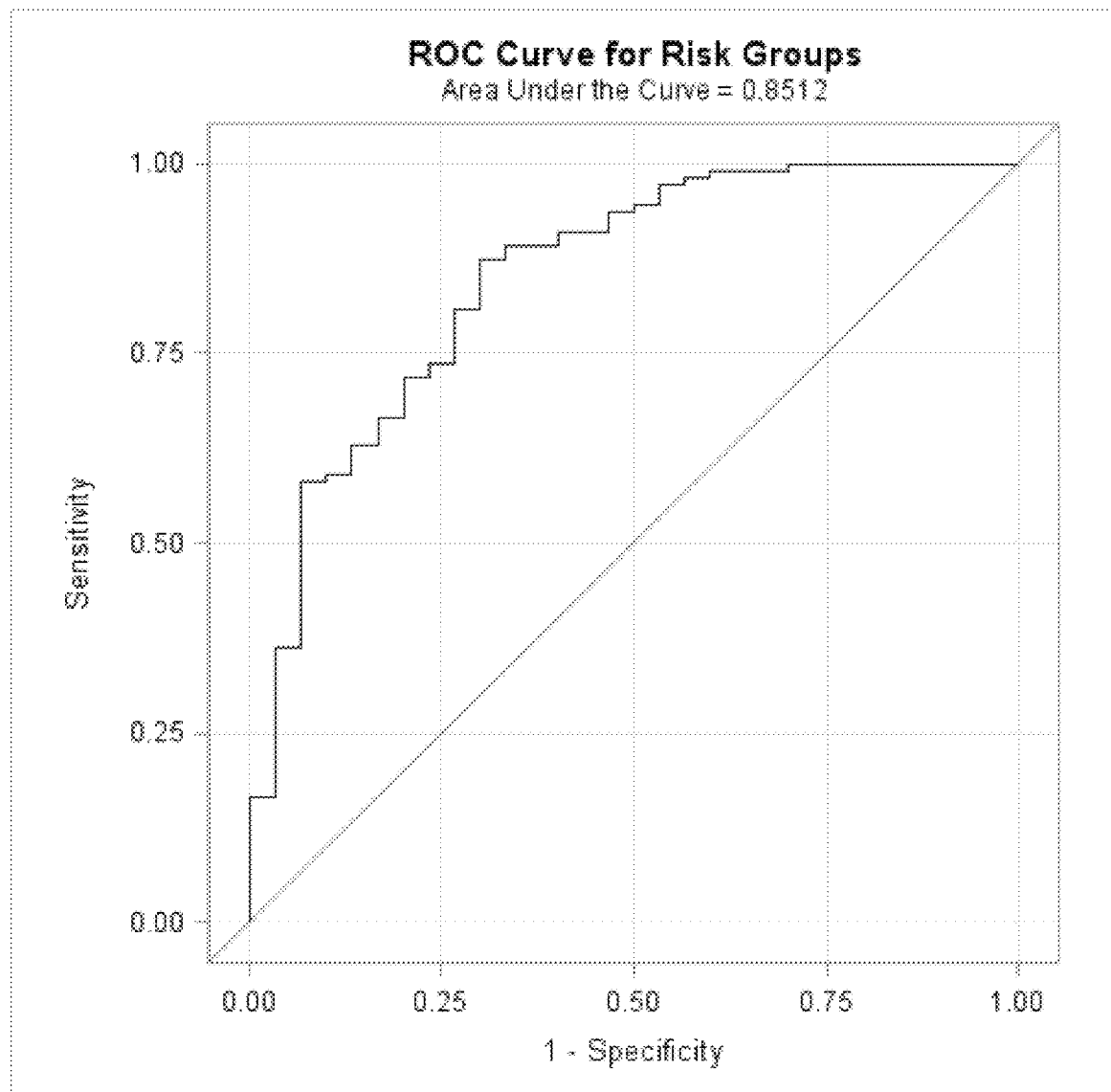
FIG. 9 illustrates the ROC curve obtained from modeling patient diagnosis (24 hours) by Multiple Logistic Regression including risk groups defined by classification tree analysis.

EvoScore demonstrated a ROC AUC of 0.8512, with 95% confidence interval of 0.770 to 0.933, with Diagnostic Sensitivity of 86.4% (designed to maximize), Specificity of 56.7%, Positive Predictive Value of 88%, Negative Predictive Value of 53.1% and Accuracy of 80% (designed to maximize) for Patients with blood drawn within 24 hours of event when comparing patients with tonic and measureable changes for seizures and epilepsy versus normal controls. The results are summarized in TABLE 8 and FIG. 9.

TABLE 8

Results of event diagnosis (24 hours).

| | P-value | AUROC | 95% CI |
|---|---|---|---|
| Tree Risk Groups + Biomarkers + Interactions | | 0.851 | 0.770, 0.933 |
| High Risk vs. Low Risk | 0.0250 | | |
| Moderate Risk vs. Low Risk | 0.0298 | | |
| Log SICAM-5 | 0.1113 | | |
| Log TARC | 0.0308 | | |
| Log TNFa | 0.3282 | | |
| TNFa/SICAM-5 | 0.0166 | | |
| Log SICAM-5 * Log TARC | 0.0291 | | |
| Log TARC* Log TNFa | 0.0540 | | |

TABLE 8-continued

Model using Predicted Probability of 0.7

|  | True Positive | True Negative | |
|---|---|---|---|
| Predicted Positive | 98 | 11 | PPV = 89.9% |
| Predicted Negative | 2 | 22 | NPV = 61.3% |
|  | Sensitivity = 89.1% | Specificty = 63.3% | |

| Model Parameters | Coefficient |
|---|---|
| Intercept | 3.05.4 |
| High Risk vs. Low Risk | 3.2836 |
| Moderate Risk vs. Low Risk | 3.157 |
| Log SICAM-5 | −47.8965 |
| Log TARC | −74.7057 |
| Log TNFa | 23.5941 |
| TNFa/SICAM-5 | 5293.4 |
| Log SICAM-5 * Log TARC | 12.0349 |
| Log TARC * Log TNFa | −8.6031 |

Example 11

Patient Diagnosis 24 hours by Multiple Logistic Regression Including Risk Groups Defined by Classification Tree Analysis Multiple Logistic regression model including risk groups defined by classification tree analysis. Results classify patients as either seizure/epileptic or normal including data from epilepsy and normal controls. The data contains samples collected within 24 hours of an event. EvoScore algorithms were determined to be a function of measurable changes of the concentration for TARC, sICAM5 and TNF-α.

Figure 10:
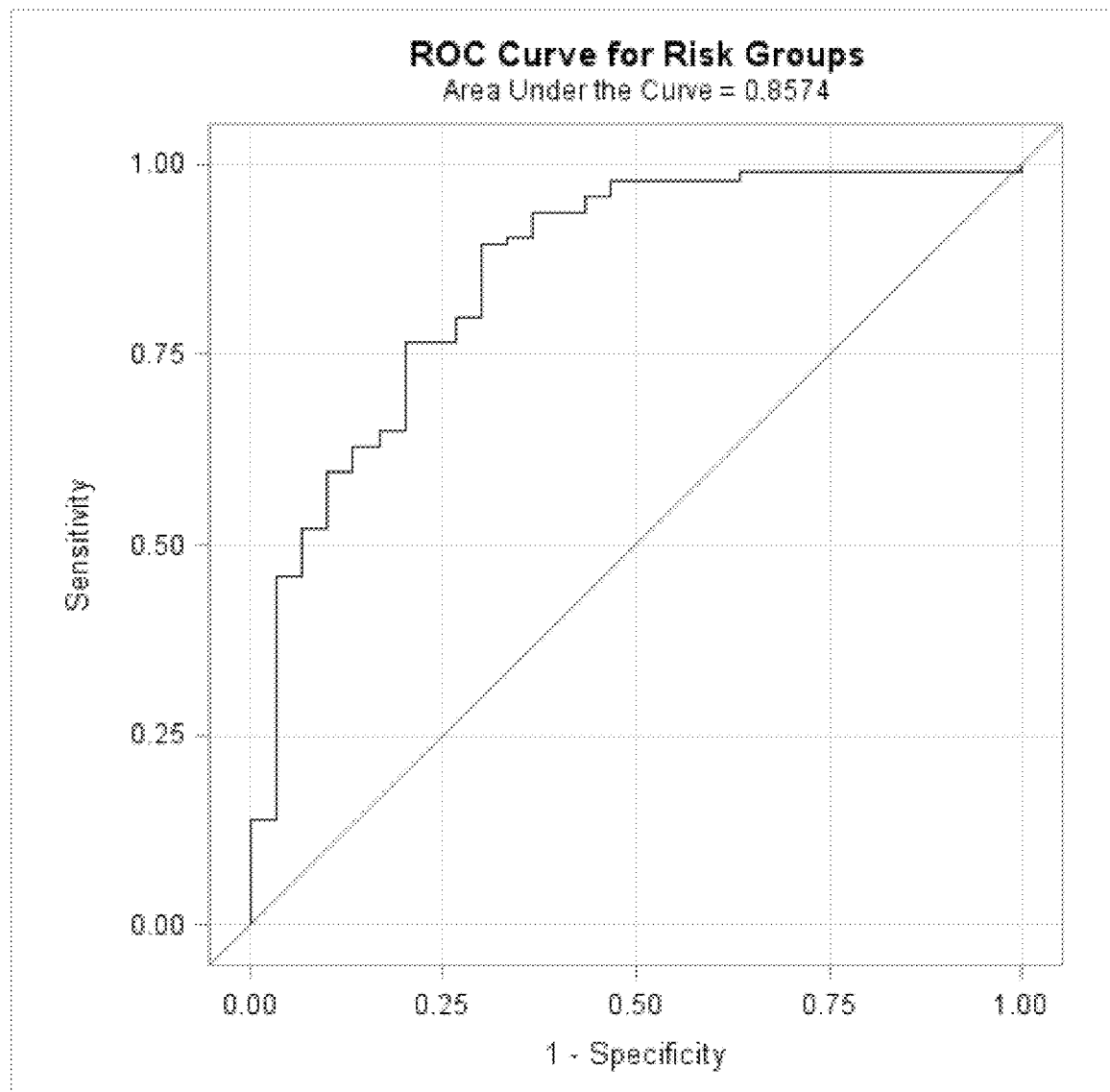
FIG. 10 illustrates the ROC curve obtained from modeling patient diagnosis (24 hours) by Multiple Logistic Regression including risk groups defined by classification tree analysis.

EvoScore demonstrated a ROC AUC of 0.8574, with 95% confidence interval of 0.776 to 0.939,with Diagnostic Sensitivity of 91.5% (designed to maximize), Specificity of 56.7%, Positive Predictive Value of 86.9%, Negative Predictive Value of 68% and Accuracy of 83.1% (designed to maximize) for Patients with blood drawn within 24 hours of event when comparing patients with tonic and measureable changes for seizures and epilepsy versus normal controls. The results are summarized in TABLE 9 and FIG. 10.

TABLE 9

Results of event diagnosis (24 hours).

|  | P-value | AUROC | 95% CI |
|---|---|---|---|
| Tree Risk Groups + Biomarkers + Interactions |  | 0.857 | 0.776, 0.939 |
| High Risk vs. Low Risk | 0.0688 |  |  |
| Moderate Risk vs. Low Risk | 0.0054 |  |  |
| Log SICAM-5 | 0.0105 |  |  |
| Log TNFa | 0.0208 |  |  |
| TARC/SICAM-5 | 0.0537 |  |  |

Model using Predicted Probability of 0.68

Model Data

|  | True Positive | True Negative | |
|---|---|---|---|
| Predicted Positive | 89 | 13 | PPV = 87.3 |
| Predicted Negative | 5 | 17 | NPV = 77.3 |
|  | Sensitivity = 94.7 | Specificty = 56.7 | |

TABLE 9-continued

| Model Parameters | Coefficient |
|---|---|
| Intercept | −42.0038 |
| High Risk vs. Low Risk | 1.9356 |
| Moderate Risk vs. Low Risk | 3.349 |
| Log SICAM-5 | 6.2204 |
| Log TNFa | −5.2289 |
| TARC/SICAM-5 | 107.4 |

Example 12

Outpatient Analysis by Multiple Logistic Regression Including Risk Groups Defined by Classification Tree Analysis For outpatients, an independent panel's diagnosis based on review of the six months of clinical care data was collected subsequent to EvoScore sampling and calculation was performed. Three independent board certified epileptologists were retained to review the diagnostic evaluations at the EMU and to confirm the diagnosis of seizure. The panel of epileptologists provided their best estimate of likely epileptic or likely non-epileptic events for this analysis, and agreement among two members of the panel will be sufficient and considered a consensus or agreed diagnosis.

For outpatients for whom the panel of at least 2 out of 3 independent reviewers agreed on a diagnosis, when applied to all-corners, including outpatients for whom there was minimal data and "unclear" epilepsy or normal, EvoScore agreed with the reviewers' consensus in diagnosing epilepsy in 77.7% of cases. This demonstrated that the test and predictive algorithms, along with in-patient data, work in all clinical settings.

Example 13

Outpatient Model by Multiple Logistic Regression Including Risk Groups Defined by Classification Tree Analysis Multiple Logistic regression model including risk groups defined by classification tree analysis. Results to classify consensus reviewed patients as either seizure/epileptic or normal controls. EvoScore algorithms were determined to be a function of measurable changes of the concentration for TARC, sICAM5 and TNF-α, as well as patient demographic characteristics including age and sex.

Figure 11:
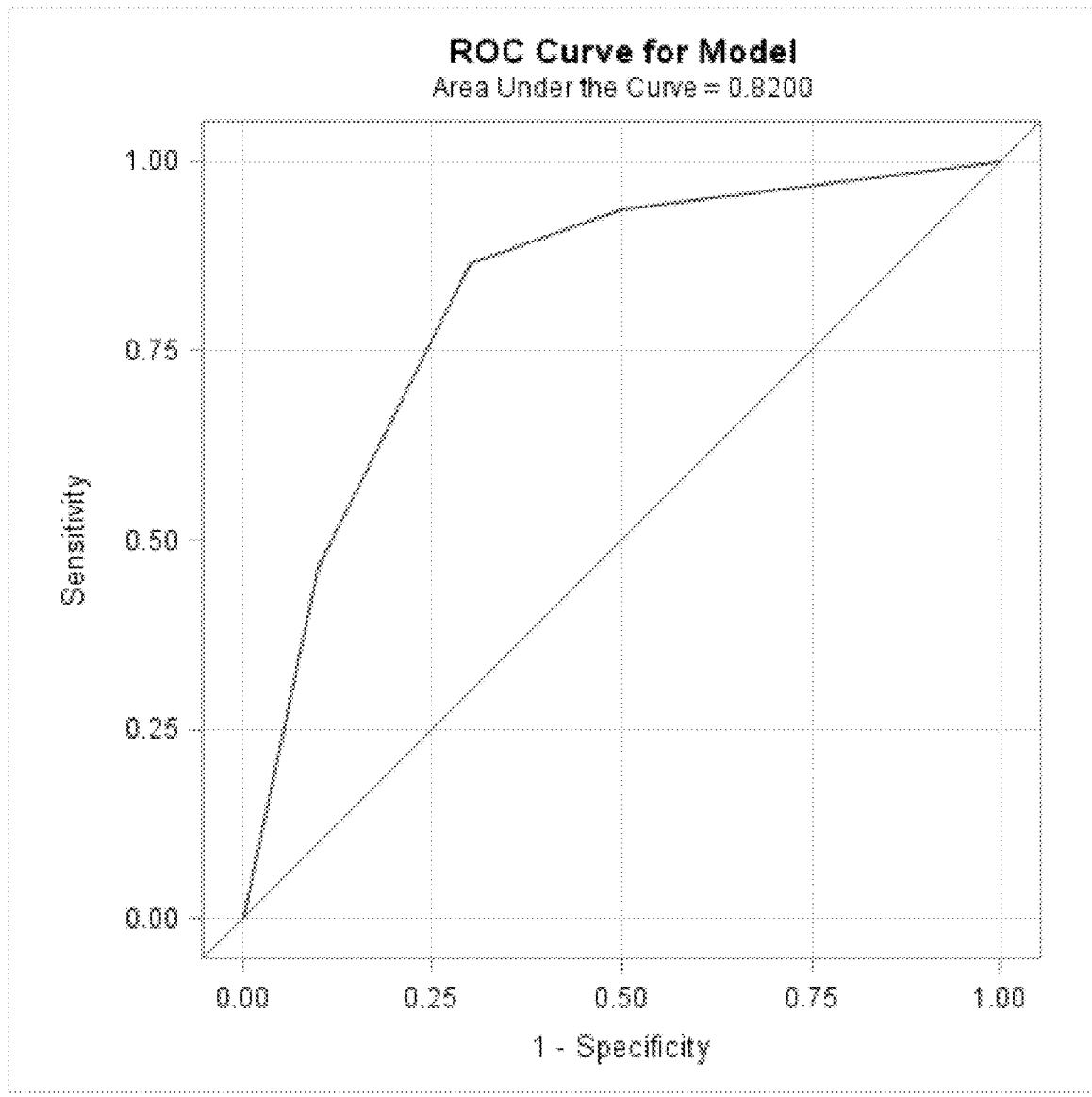
FIG. 11 illustrates the ROC curve obtained from modeling outpatient results by Multiple Logistic Regression including risk groups defined by classification tree analysis.

EvoScore demonstrated a ROC AUC of 0.8200, with 95% confidence interval of 0.731 to 0.909, with Diagnostic Sensitivity of 86.4% (designed to maximize), Specificity of 70%, Positive Predictive Value of 92.3% and Negative Predictive Value of 55.3% for Patients with blood drawn when comparing patients with tonic and measureable changes for seizures and epilepsy versus normal controls. The results are summarized in TABLE 10 and FIG. 11.

TABLE 10

Outpatient Model

|  | P-value | AUROC | 95% CI |
|---|---|---|---|
| Tree Risk Groups + Biomarkers + Interactions |  | 0.820 | 0.731, 0.909 |
| High Risk vs. Low Risk | <0.0001 |  |  |
| Sex | 0.0601 |  |  |

TABLE 10-continued

| | Model Data | | |
|---|---|---|---|
| | True Positive | True Negative | |
| Predicted Positive | 108 | 9 | PPV = 92.3 |
| Predicted Negative | 17 | 21 | NPV = 55.3 |
| | Sensitivity = 86.4 | Specificty = 70.0 | |

| Model Parameters | Coefficient |
|---|---|
| Intercept | −0.1197 |
| High Risk vs. Low Risk | 2.6776 |
| Sex | −0.4726 |

Example 14

EEG and EvoScore

EEG was demonstrated to have a Sensitivity of 37%, Specificity of 99%, PPV of 98%, and NPV of 66%. We found that EEG may miss seizure events, resulting in significant false negatives and corresponding potential under-treatment of epilepsy patients. Our results are reflective of the recognized range of this test (Sensitivity of 25-56%, and Specificity of 78%-98%). EvoScore demonstrated better sensitivity and negative predictive value, and near equivalent specificity and positive predictive value when evaluating phasic changes versus EEG. EvoScore can be used in combination with EEG for patient diagnosis and treatment. Additionally, EvoScore can be used in combination with other diagnostic and test approaches as defined herein.

Example 15

Technical Reproducibility and Quality Control

It has been confirmed that:
1) Repeated freeze-thaw of plasma samples does not affect TARC, sICAM5, and TNFα levels
2) Test-test reproducibility for same samples is nearly 100%
3) Varying plasma dilutions do not alter relative TARC, sICAM5, and TNFα levels
4) Long-term storage (up to 1 year) does not alter TARC, sICAM5, and TNFα levels
5) The test can be run optimally in ~6 hours, but can be optimized for various workflows in laboratory environments
6) Batch-to-batch variability is minimal
7) Full methodologies have been optimized into "Standard Operating Procedures" to insure consistent assay techniques from batch to batch.

Example

Summary

Based on the above examples: (1) Biomarkers alone including TARC and sICAM5, and the ratio of biomarkers TNFα/TARC and TNFα/sICAM5 were demonstrated to have statistically significant differences (p<0.05) between Normal Controls and Event Diagnosis, between Normal Controls and Patient Diagnosis 1, and between Normal Controls and Patient Diagnosis 1 & 2. These biomarkers and ratios of biomarkers can be used alone or in combination for the determination of seizure or not and epilepsy or not; (2) At 24 hours, EvoScore can tell the difference between a seizure and a normal control individual ("phasic changes"); (3) At 24 hours, EvoScore can tell the difference between an epilepsy patient and a normal control individual ("tonic changes"); (4) EvoScore is at least equal to or better than EEG in assessing phasic changes between a seizure and normal controls; (5) EvoScore can be used in combination with EEG and or other tests for diagnostic and treatment assessment; (6) in the "all corners" outpatient analysis of 240 patients, EvoScore can identify patients with seizures in 83% of cases; and (7) EvoScore can tell the difference between a seizure and a normal control ("phasic changes"), and between an epilepsy patient and a normal control ("tonic changes")for samples taken greater than 24 hours from the event, including the potential for 72 hours or greater; and (8) the test is robust to be run in any clinical or healthcare setting and in laboratory conditions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The mathematical coefficients and algorithms provided herein are illustrative and exemplary and are provided for the purpose of illustration only. The disclosure encompassed herein should in no way be construed as being limited to these examples of coefficients and algorithms, but rather should be construed to encompass any and all variations which become evident as a result of the teachings provided herein. In particular, alternative coefficients and algorithms may become apparent as a result of the use of different clinical data.

Although the invention has been described in conjunction with specific embodiments thereof, it is evident that many alternatives, modification and variations will be apparent to those skilled in the art. Accordingly, it is intended to embrace all such alternatives, modification and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Any document (including but not limited to any patent, patent application, publication, and website) listed herein is hereby incorporated herein by reference in its entirety. While these developments have been disclosed with reference to specific embodiments, it is apparent that other embodiments and variations of this invention are devised by others skilled in the art without departing from the true spirit and scope of the developments. The appended claims include such embodiments and variations thereof.

The invention claimed is:
1. A method of treating a seizure disorder in a patient, the method comprising:
  obtaining a blood plasma or blood serum sample from the patient;

measuring or detecting the concentration of thymus and activation-regulated chemokine (TARC) in the blood plasma or blood serum sample via at least one selected from the group of enzyme-linked immunoassay (ELISA), Indirect ELISA, Sandwich ELISA, Competitive Elisa, Multiple and Portable (M&P) ELISA, and combinations thereof;

measuring or detecting the concentration of tumor necrosis factor alpha (TNF-α) in the blood plasma or blood serum sample via at least one selected from the group of enzyme-linked immunoassay (ELISA), Indirect ELISA, Sandwich ELISA, Competitive Elisa, Multiple and Portable (M&P) ELISA, and combinations thereof;

comparing concentrations of TARC and TNF-α to normal control concentrations of TARC and TNF-α, respectively;

determining at least one of the following: i) the concentration of TARC in the blood plasma or blood serum sample obtained from the patient is increased compared to the normal control concentration of TARC; and ii) the concentration ratio of TNF-α to TARC in the blood plasma or blood serum sample obtained from the patient is decreased compared to the normal control concentration ratio of TNF-α to TARC;

diagnosing the seizure disorder in the patient; and administering a therapy for epilepsy to the patient, wherein the therapy for epilepsy is a therapeutically effective dose of an anti-epileptic compound selected from the group consisting of phenytoin, fosphenytoin, midazolam, pregabalin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis based drugs and pharmaceutically acceptable salts, prodrugs, and derivatives thereof.

2. The method of claim 1, wherein the normal control concentrations of TARC and TNF-α are obtained from a subject that has at least one characteristic selected from (i)-(iii):
  (i) the same sex as the patient,
  (ii) the same age or a similar age as the patient, or
  (iii) the same race as the patient.

3. The method of claim 1, further comprising using electroencephalography (EEG) to diagnose the seizure disorder in the patient.

4. The method of claim 1, further comprising using magnetic resonance imaging (MRI), complete blood count (CBC), chemistry metabolic panel (CMP), a toxicology screen test, a positron emission tomography (PET) scan, a lumbar puncture, or a combination thereof to diagnose the seizure disorder in the patient.

5. The method of claim 1, further comprising:
  measuring or detecting the concentration of soluble intercellular adhesion molecule 5 (sICAM-5) in the blood plasma or blood serum sample via at least one selected from the group of enzyme-linked immunoassay (ELISA), Indirect ELISA, Sandwich ELISA, Competitive Elisa, Multiple and Portable (M&P) ELISA, and combinations thereof; and
  comparing the concentration of sICAM-5 to a normal control concentration of sICAM-5.

6. The method of claim 5, further comprising determining the concentration of sICAM5 in the blood plasma or blood serum sample obtained from the patient is increased compared to the normal control concentration of sICAM5.

7. The method of claim 5, further comprising determining the concentration ratio of TNF-α to sICAM5 in the blood plasma or blood serum sample obtained from the patient is decreased compared to the normal control concentration ratio of TNF-α to sICAM5.

\* \* \* \* \*